(12) United States Patent
Sadakane et al.

(10) Patent No.: US 7,347,622 B2
(45) Date of Patent: Mar. 25, 2008

(54) X-RAY CT SCANNER AND SCAN METHOD

(75) Inventors: Tomoyuki Sadakane, Kyoto (JP); Masakazu Suzuki, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 11/491,354

(22) Filed: Jul. 21, 2006

(65) Prior Publication Data

US 2007/0041491 A1    Feb. 22, 2007

(30) Foreign Application Priority Data

Jul. 22, 2005  (JP) .......................... P2005-213057

(51) Int. Cl.
    *H05G 1/02* (2006.01)
(52) U.S. Cl. ........................ 378/197; 378/39
(58) Field of Classification Search ................ 378/4, 378/10, 20, 38–40, 11, 15, 19, 193, 195, 196, 378/197

See application file for complete search history.

(56) References Cited

U.S. PATENT DOCUMENTS

2001/0036246 A1* 11/2001 Graumann ................. 378/39
2002/0122537 A1*  9/2002 Yoshimura ................ 378/208

* cited by examiner

*Primary Examiner*—Courtney Thomas
(74) *Attorney, Agent, or Firm*—William L. Androlia; H. Henry Koda

(57) ABSTRACT

In an X-ray CT scan, a distance between an X-ray generator and a rotation center and/or a distance between a X-ray detector and the rotation center can be changed according to a magnification of an image. A rotary device has an X-ray generator and an X-ray detector opposing to each other, provided to interpose an object between them. A rotary mechanism rotates the rotary device around a rotary axis, and a movement mechanism moves the rotary axis or the object in a plane perpendicular to the rotary axis. The rotation center in a viewpoint of CT scan different from the rotary axis is always kept at a point in a region of interest in the object according to a motion synthesized from the rotation of the rotary device and the movement of the rotary axis or the object.

12 Claims, 15 Drawing Sheets

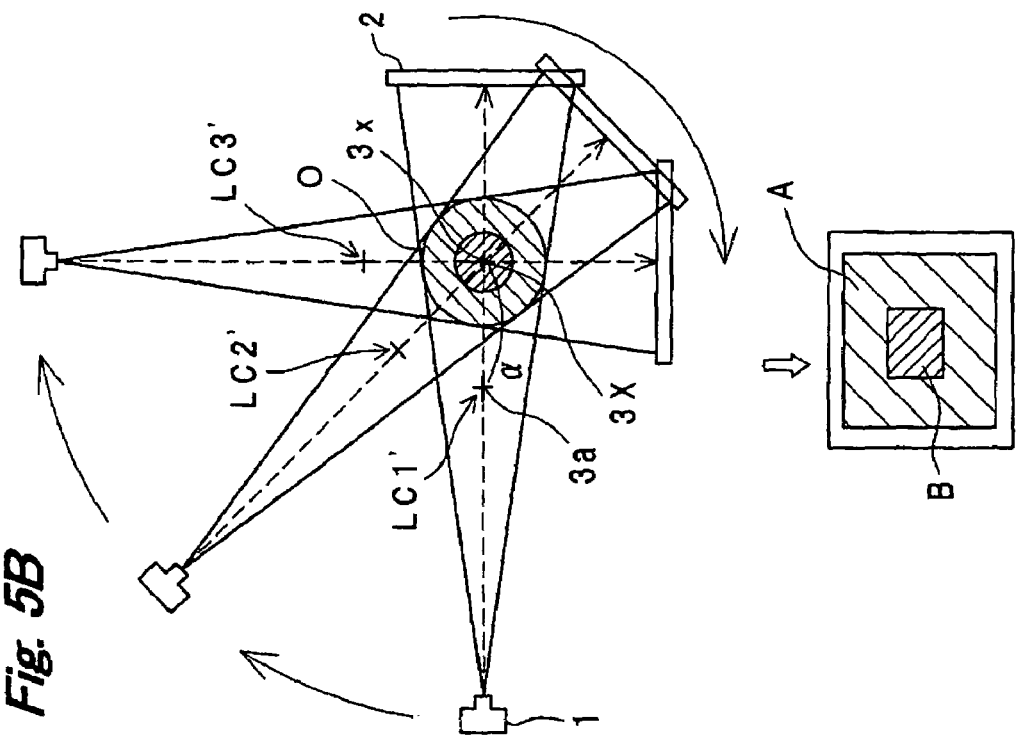
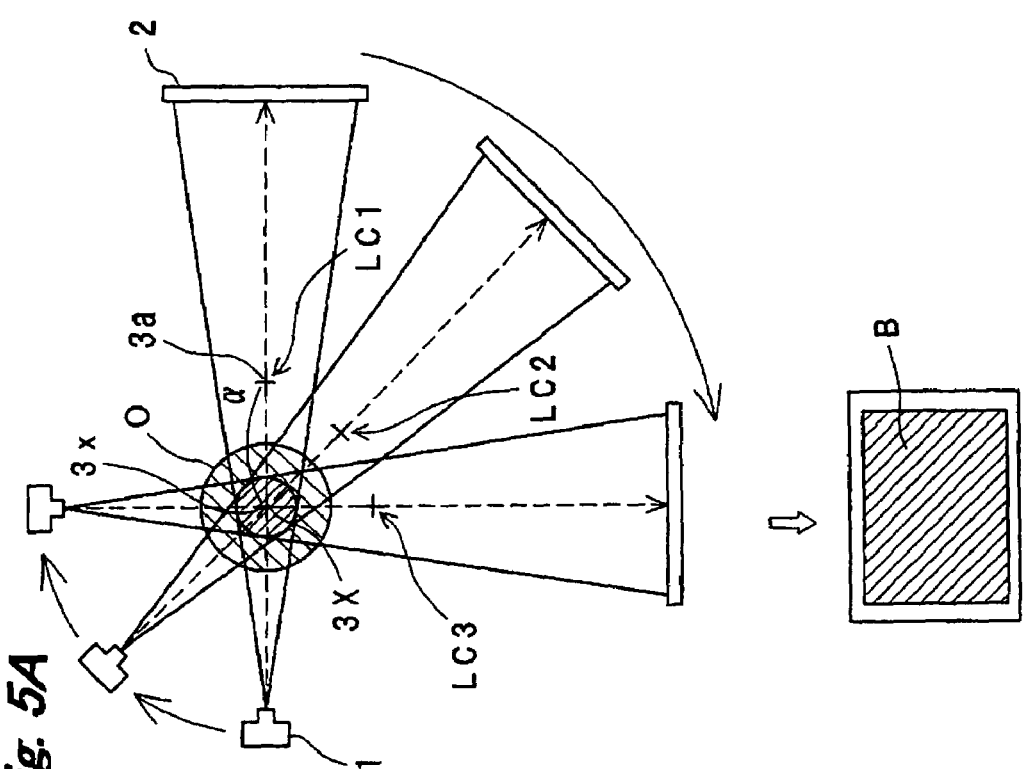

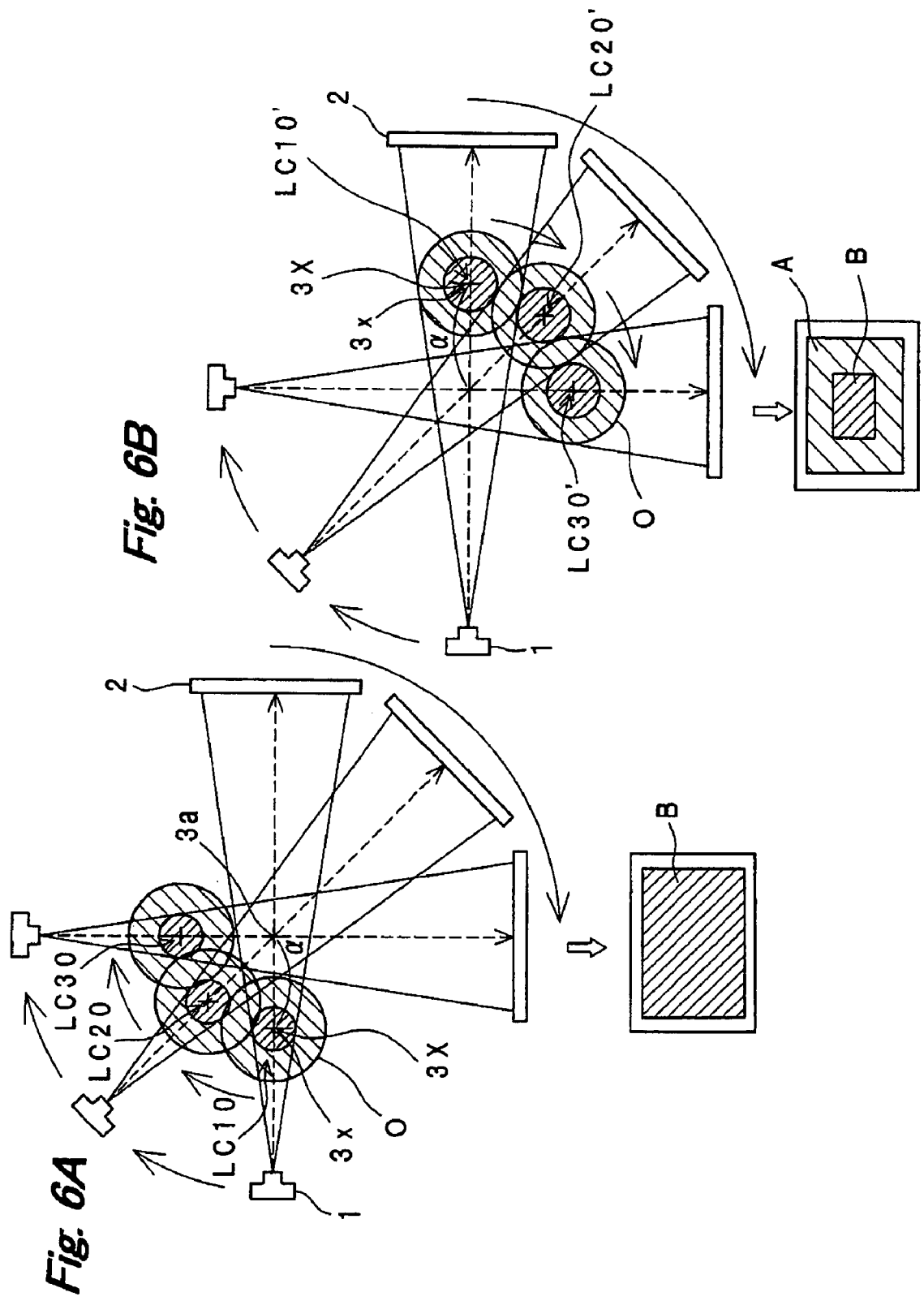

X-RAY CT SCANNER AND SCAN METHOD

FIELD OF THE INVENTION

The invention relates to X-ray computer tomography for reconstructing an image in a three-dimensional region.

BACKGROUND ART

In an X-ray computer tomography (CT) scanner, an object is positioned between an X-ray generator and an X-ray detector. The X-ray generator and the X-ray detector are rotated around the object, and the object is exposed to an X-ray beam generated by the X-ray generator beam in many directions. The X-ray intensity distribution transmitting the object (or a projection of the object) is measured with the X-ray detector. Based on the X-ray projection data acquired in one rotation, a distribution of linear absorption coefficients (or an image) inside the object is reconstructed two-dimensionally to create a slice image of the object. The reconstruction calculation is performed on a plurality of planes perpendicular to the rotary axis, to create a three-dimensional image based on the slice images.

If a magnification of an image can be changed in a CT scan, a field of view (a size of a region of interest) can be changed, and a resolution of the image can be changed. In an X-ray CT scanner having an X-ray generator and an X-ray detector fixed to a rotary arm or a gantry, the X-ray generator and the X-ray detector are rotated around an object while keeping the distances among the X-ray generator, the object and the X-ray detector constant. The magnification of an image can be increased or decreased according to the relative distance between the X-ray generator or X-ray detector and the object.

As will be explained later, a distance between the X-ray generator and a rotation center for CT scan and/or a distance between the X-ray detector and the rotation center can be changed relatively in this invention. This is relevant to some prior art documents. In a CT scanner described in Japanese Patent laid open Publication 2004-329293, transmission still images (called as scout images) are taken in two positional relationships between the X-ray generator and the X-ray detector before starting a CT scan, in order to determine a three-dimensional position of a region to be scanned. When the size of a scout image is changed, the position of a chair is moved relative to the X-ray detector. However, though the size of a scout image can be changed, a structure for changing the magnification of an image is not described. In a CT scanner described in Japanese Patent laid open Publication H5-322802/1993 to be used for an object in industrial fields, the positions of the X-ray generator and the X-ray detector are fixed. On the other hand, an object is put on a table, and a projection image of the object is taken while the table is rotated. The magnification of the image is changed according to the positions of the X-ray generator and the X-ray detector relative to the rotating table. However, the rotation of the object is possible because the object is a matter. When the object is a person, problems such as artifacts due to his or her motions and dizziness caused by the rotation occur. Therefore, it cannot be adopted practically for CT scan of a person, especially for medical areas. Further, even when the object is a matter, the CT scanner cannot be used if the object has a structure so precise as not to be subjected to continuous rotation. In an X-ray CT scanner described in Japanese Patent laid open Publication 2001-37747, a rotary arm has an X-ray generator and an X-ray planar detector opposing to each other, and an object is arranged between them. The X-ray planar detector is mounted to a ring arm with an extensible arm, and the detector can be set nearer or farther from the object so that a magnification of an image can be changed. However, a mechanism for moving the X-ray detector relative to the rotation device or for moving the rotation device relative to the X-ray device is necessary to change the magnification. Medical devices are used widely for panorama X-ray imaging or for X-ray CT scan wherein an X-ray generator and an X-ray detector are provided at two ends of a rotary arm, and it is desirable to modify them.

SUMMARY OF THE INVENTION

An object of the invention is to change a field of view of CT scan (or a size of a region of interest) more easily.

A first X-ray CT scanner according to the invention has a rotary device comprising an X-ray generator and an X-ray detector opposing to each other and interposing an object between them, a rotary mechanism for rotating the rotary device around a rotary axis, a mechanism for moving the rotary axis of the rotary mechanism in two-dimensional directions crossing the rotary axis, and a controller which controls the rotary mechanism and the mechanism for moving the rotary axis, to rotate the rotary device so as to keep a center of a region of interest in the object always at a rotation center in a viewpoint of CT scan due to a synthesized motion of the rotation of the rotary device by the rotary mechanism and the movement of the rotary axis by the mechanism for moving the rotary axis. A distance between the X-ray generator and the rotation center and/or a distance between the X-ray detector and the rotation center can be changed so that magnification can be changed.

According to the first X-ray CT scanner and according to second and third X-ray CT scanners and an X-ray CT scan method to be explained later, a field of view (or a magnification of a region of interest) can be changed easily by using the X-ray generator and the X-ray detector in the relative positional relationship in a CT scan. Especially, when the X-ray detector has a detection area with a limited area, if the region of interest as a magnification is too large for the detection area or the entire region of interest cannot be imaged, the magnification can be decreased so that the entire region of interest fits the detection area.

Further, the magnification can be changed without using a mechanism for moving the X-ray detector or the X-ray generator relative to the rotary device.

Further, when the rotary device is moved around the rotary axis, even if a deviation of the position of the axis happens due to a mechanical malfunction, it can be corrected easily by setting the rotation center different from the rotary axis.

Preferably, in the X-ray CT scanner, the mechanism for moving the rotary axis comprises a first moving device which moves the rotary axis of the rotary mechanism in a first direction different from the rotary axis, and a second moving device which moves the rotary axis in a second direction different from the first direction and from the rotary axis. Thus, two-dimensional movement of the object can be controlled easily.

Preferably, in the X-ray CT scanner, the mechanism for moving the rotary axis and the rotary device are mounted in the same housing. Thus, a rotary mechanism can be set in a space which is rather wide two-dimensionally for containing the mechanism for moving the rotary axis. Further, because the rotary mechanism is not needed to be provided in the rotary device, the structure of the rotary device can be simplified.

Preferably, in the X-ray CT scanner, the mechanism for moving the rotary axis comprises one link member or a plurality of link members connected in series connected to a bearing of the rotary mechanism, whereby the rotation center can be moved in two-dimensional directions crossing the rotary axis. Then, the two-dimensional movement of the rotary axis can be controlled with a simple structure.

A second X-ray CT scanner according to the invention has a rotary device comprising an X-ray generator and an X-ray detector opposing to each other and interposing an object between them, a rotary mechanism for rotating the rotary device around a rotary axis, a mechanism for moving the object around the rotary axis in two-dimensional directions crossing the rotary axis, and a controller which controls the rotary mechanism and the mechanism for moving the object, to rotate the rotary device so as to keep a point in a region of interest in the object always at a rotation center in a viewpoint of CT scan due to a synthesized motion of the rotation of the rotary device by the rotary mechanism and the movement of the object. Thus, a distance between the X-ray generator and the rotation center and/or a distance between the X-ray detector and the rotation center can be changed so that magnification can be changed.

Preferably, in the second X-ray CT scanner, the mechanism for moving the object has a first moving device which moves the object in a first direction different from the rotary axis, and a second moving device which moves the object in a second direction different from the first direction and from the rotary axis. Then, two-dimensional movement of the object can be controlled easily.

Preferably, in the second X-ray CT scanner, the rotary axis of the rotary mechanism extends vertically. Then, if the object is a human body, it can be put in a standing position or in a sitting position, and the scanner can be installed in a small space.

Preferably, in the first and second X-ray CT scanner, the rotary axis is a rotary arm. Then, the rotary axis can be provided in a mechanically simple structure.

A third X-ray CT scanner according to the invention has a rotary device comprising an X-ray generator and an X-ray detector opposing to each other and interposing an object between them, a rotary mechanism for rotating the rotary device around a rotary axis, a mechanism for moving the rotary axis of the rotary mechanism and/or the object in two-dimensional directions crossing the rotary axis, and a controller which controls the rotary mechanism and the mechanism for moving the rotary axis and/or the object, to rotate the rotary device so as to keep a point in a region of interest in the object always at a rotation center in a viewpoint of CT scan due to a synthesized motion of the rotation of the rotary device by the rotary mechanism and the movement of the rotary axis and/or the object by the mechanism for moving the rotary axis and/or the object.

In an X-ray CT scan method according to the invention, a distance between the X-ray generator and the rotation center and/or a distance between the X-ray detector and the rotation center to change magnification is changed in an X-ray CT scanner having a rotary device comprising an X-ray generator and an X-ray detector opposing to each other and interposing an object between them, a rotary mechanism for rotating the rotary device around a rotary axis, a mechanism for moving the rotary axis of the rotary mechanism in two-dimensional directions crossing the rotary axis, and a controller which controls the rotary mechanism and the mechanism for moving the rotary axis, to rotate the rotary device so as to keep a point in a region of interest in the object always at a rotation center in a viewpoint of CT scan due to a synthesized motion of the rotation of the rotary device by the rotary mechanism and the movement of the rotary axis by the mechanism for moving the rotary axis.

BRIEF DESCRIPTION OF THE DRAWINGS

These and other objects and features of the present invention will become clear from the following description taken in conjunction with the preferred embodiments thereof with reference to the accompanying drawings, and in which:

FIGS. 5A and 5B are diagrams for explaining the first X-ray scanner for enlargement and for reduction, FIGS. 6A and 6B are diagrams for explaining the second X-ray scanner for enlargement and for reduction.

DESCRIPTION OF PREFERRED EMBODIMENTS

Figure 1A:
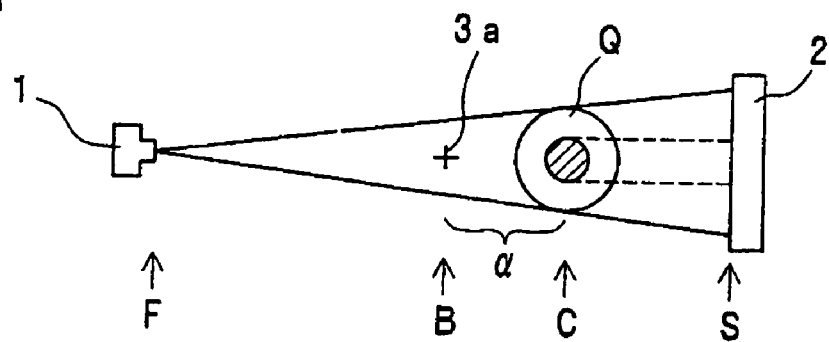
FIGS. 1A, 1B and 1C are sectional views for illustrating a structure of a recording medium of an embodiment of the invention.

Embodiments of the invention are explained below with reference to the appended drawings, wherein like reference characters designate like or corresponding parts throughout the several views.

In an X-ray CT scanner, a rotary device such as a rotary arm has an X-ray generator 1 and an X-ray detector 2 opposing to each other while interposing an object between them. The distance between the X-ray generator 1 and the X-ray detector 2 is constant. A rotary mechanism supports the rotary device so as to be rotatable around a rotary axis in the rotary mechanism. The rotary axis is referred to as "mechanical rotary axis" or simply as "rotary axis". The mechanical rotary axis or rotary axis can be set, for example, by use of a rotary shaft because a rotary shaft having the rotary axis is used for rotation by the rotary mechanism. Any rotary mechanism can be used to rotate at least an X-ray generator 1 and an X-ray detector 2. Even if the rotary mechanism has no mechanical shaft, it has a rotary axis around which the X-ray generator 1 and the X-ray detector 2 are rotated. For example, a ring shaped rotary device having an X-ray generator 1 and an X-ray detector 2 opposing each other and driven by a motor through a rotor or gears, without a rotary shaft, can be used, and it has a rotary axis. When the rotary device is rotated around the mechanical rotary axis, the X-ray generator 1 and the X-ray detector 2 are rotated around the object. It is preferable that the mechanical rotary axis is perpendicular or substantially perpendicular to the center line of an X-ray beam emitted by the X-ray generator 1. In this case, if the object is a human body, it can be in a standing position or in a sitting position, and the scanner can be installed in a small space.

A magnification (or a magnifying power) of an image acquired in an X-ray CT scan is explained here. In FIG. 1, F is a position of the X-ray generator 1 (precisely a position of a focal point of X-ray beam in the X-ray generator 1), S is a position of the X-ray detector 2 (precisely a position of an X-ray detection plane in the X-ray detector 2), B is a position of the rotary shaft 3$a$ in the rotary mechanism, and C is a position of the object O (precisely a position of a point in a region of interest in the object).

In the cases to be mentioned below, a region in a cylindrical or almost cylindrical form always irradiated by the X-ray cone beam is regarded as a region of interest. (The region in a cylindrical or almost cylindrical form is, for example, region B in FIG. 5A or region A in FIG. 5B which can be scanned in CT scan by rotation of the X-ray cone beam.) A position of the center of the rotation of the X-ray cone beam can be regarded as the center of the region of interest observed from the viewpoint in direction of the rotary axis, and a point namely the center of the region of interest can be chosen as the position C. However, there is a case in that the form of the region of interest is not fixed. In this case, a point at will in the region of interest in a non-fixed form can be chosen as position C. In another case in that a size of the region to be scanned is so small as enclosed enough in the region in cylindrical or almost cylindrical form mentioned above, the region which can at least enclose the region to be scanned can be regarded as a region of interest. In this case a position of the center of the rotation of the X-ray cone beam can be chosen as position C, and of course a position of the center of the rotation of the X-ray cone beam can be chosen as the position C.

Figure 1B:
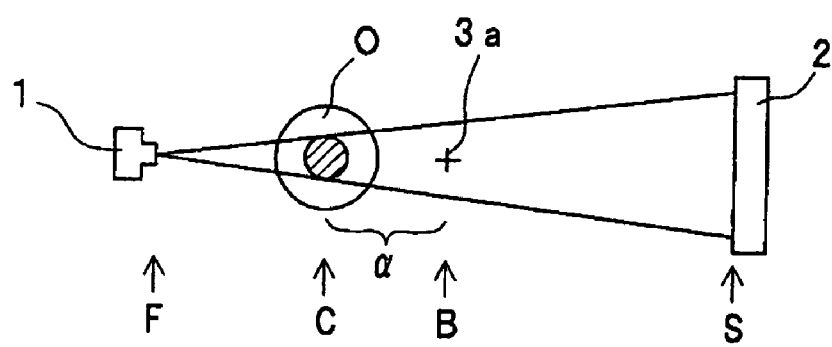
Figure 1C:
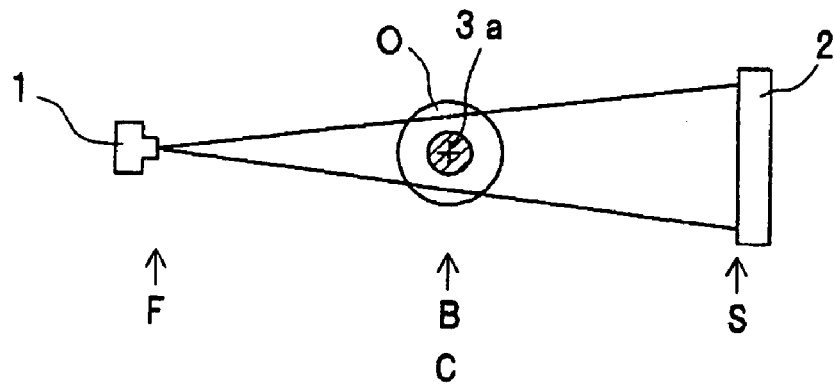

As shown in FIG. 1C, if the position B of the rotary shaft 3$a$ in the rotary mechanism coincides with the position C of the point in the region of interest in the object O, the magnification of the object in an imaging plane of the X-ray detector 2 is expressed as FS/FB (=FS/FC) with use of distance FS between the X-ray generator 1 and the X-ray detector 2 and distance FB between the X-ray detector 1 and the rotary shaft 3$a$. (In FIG. 1C, distance FB=distance FC between the X-ray detector 1 and the object O.)

The magnification can be changed by changing the distance FC between the X-ray generator 1 and the object O and/or the distance CS between the object O and the X-ray detector 2. For example, as shown in FIG. 1A, when the position C of the object O is changed relative to the rotary shaft 3$a$ in the rotary mechanism towards the X-ray detector 2, the magnification becomes smaller, and a larger region can be imaged. In this situation, the object O is moved towards the X-ray detector 2 relative to the X-ray detector 2 by distance $\alpha$ (>0) before an X-ray CT scan. Next, as will be explained later with reference to FIG. 2, the rotary device 3 is rotated, while the rotation center of the rotary mechanism or the rotary shaft 3$a$ is moved along a circular orbit of a radius a having its center at the point 3X in the region of interest in the object 1 (strictly speaking, the position at the rotation center in FIG. 1A). Alternatively, as will be explained later with reference to FIG. 3, the object O is moved along a circular orbit of a radius a having its center at the rotation center of the rotary mechanism. The center of the rotation of the rotary mechanism is at the rotary shaft 3$a$, and the magnification of the object O imaged in the X-ray detector 2 is FS/(FB+$\alpha$) (=FS/FC).

On the other hand, as shown in FIG. 1B, when the position C in the object O is changed relative to the rotary shaft 3$a$ in the rotary mechanism towards the X-ray generator 1, the magnification becomes larger, and a smaller region can be imaged. In this situation, the object O is moved towards the X-ray generator 1 by distance $\alpha$ (>0) before an X-ray CT scan. Next, as will be explained later with reference to FIG. 2, the rotary device 3 is rotated, and the rotation center of the rotary mechanism or the rotary shaft 3$a$ is moved along a circular orbit of a radius a having its center at the point in the region of interest in the object O, or, as will be explained later with reference to FIG. 3, the object O is moved along a circular orbit of a radius a having its center at the rotation center of the rotary mechanism. The center of the rotation of the rotary mechanism is at the rotary shaft 3$a$, and the magnification of the object O imaged in the X-ray detector 2 is FS/(FB−$\alpha$) (=FS/FC).

In the situations shown in FIGS. 1A and 1B, the rotary shaft 3$a$ in the rotary mechanism (position B) does not coincide with the point in the region of interest in the object O (position C). Therefore, when the rotary mechanism makes the rotary device 3 rotate around the rotary shaft 3$a$, the position of the rotary shaft 3$a$ in the rotary mechanism or an object O has to be moved circularly according to the rotation angle of the rotary mechanism. If this circular motion is realized, the magnification in a CT scan can be changed. Then, the entire rotary mechanism should be subjected to a circular rotation according to the rotation angle of the rotary mechanism. Thus, the relative positional relationship among the X-ray generator 1, an orbit O and the X-ray detector 2 is kept constant. Such a CT scan has following advantages. By using the X-ray generator 1 and the X-ray detector 2 in the relative positional relationship, a field of view or a magnification of a region of interest can be changed easily. Especially, when the X-ray detector 2 has a detection area with a limited size, if the region of interest at a magnification is too large for the detection volume or the entire region of interest to be imaged, the magnification can be decreased so that the entire region of interest fits the detection area. Further, the magnification can be changed without using a mechanism for moving the X-ray detector 2 or the X-ray generator 1 relative to the rotary device. Even if a deviation of the position of the rotary axis arises due to a mechanical malfunction or the like when the rotary device is moved around the rotary shaft, it can be corrected easily by setting a rotation center in a viewpoint of CT scan different from the mechanical rotary axis. The viewpoint of CT scan may also be called as a viewpoint of taking a photograph of the object with the detector 2, and the rotation center in a viewpoint of taking a photograph is different from the mechanical rotary axis, as mentioned above on the rotation center in a viewpoint of CT. The rotation center in the viewpoint of CT scan is also explained later.

Figure 2:
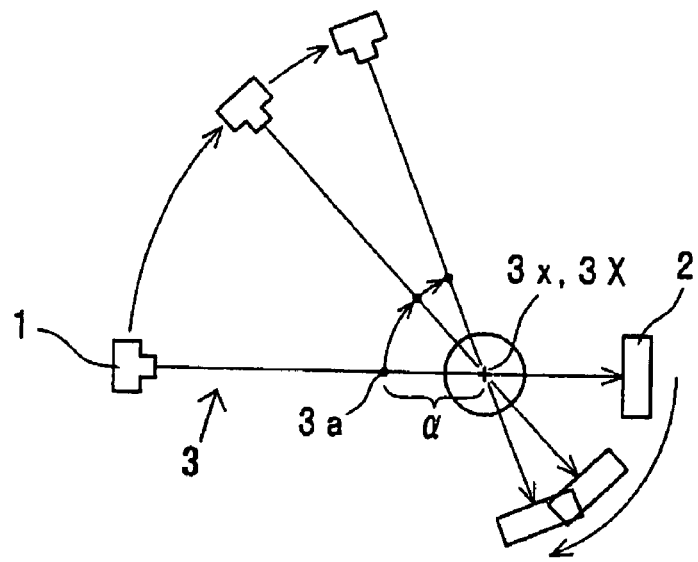
FIG. 2 is a schematic diagram for explaining a situation wherein a magnification is changed while a rotary device is rotated circularly.

First, a first X-ray CT scanner is explained. In the first X-ray CT scanner, a mechanism 31, which will be explained later in detail, is provided for moving the rotary shaft 3a of the rotary mechanism in two-dimensional directions crossing the rotary shaft 3a. FIG. 2 shows a situation of the control. This mechanism 31 moves the rotary shaft 3a. The rotary device 3 rotates the X-ray generator 1 and the X-ray detector 2 around the rotary shaft 3a, while the rotary shaft 3a is moved by the mechanism 31. The two types of motions are synchronized so that the distance FC between the X-ray generator 1 and the point 3X in the region of interest and the distance CS between the X-ray detector 2 and the center 3X are always kept constant. In the synthesized motion due to the two types of motion, a rotation center 3X in a viewpoint of CT scan is at the point 3X in the region of interest in the object O, and the X-ray generator 1 and the X-ray detector 2 are rotated around the center 3X to keep the distance to the center 3X always constant. When the X-ray generator 1 and the X-ray detector 2 are rotated by an angle around the rotary shaft 3a, the rotary shaft 3a is also rotated by the same angle around the point 3X in the region of interest. Then, when viewed from the point 3X in the region of interest, the X-ray generator 1 and the X-ray detector 2 are rotated around the center 3X, similarly to a conventional CT scan shown in FIG. 1C though the position of the object is different from the rotary shaft. Thus, even when the rotary shaft 3a of the rotary mechanism has a position different from the point 3X in the region of interest in the object O, the rotation center 3X different from the rotary shaft 3a is always set to the point 3X of the region of interest, and the rotary device 3 is always rotated around the point 3X in the region of interest in the object O, due to the synthesized motion which links the rotation of the rotary device 3a of the rotary mechanism with the movement of the rotary shaft by the mechanism 31 for moving the rotary shaft.

Figure 3:
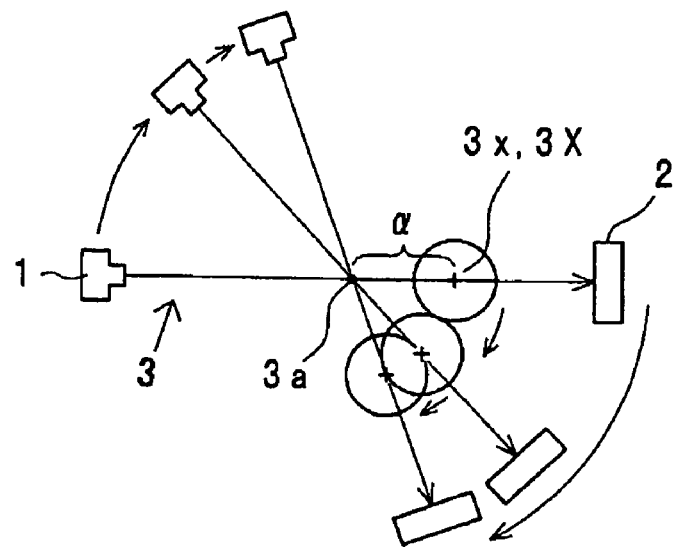
FIG. 3 is a schematic diagram for explaining a situation wherein the magnification is changed while an object is rotated circularly.

The above-mentioned "rotation center 3X in a viewpoint of CT scan different from the rotary shaft 3a" represents a rotation center defined independently of the rotary shaft 3a in a viewpoint of CT scan, and it is realized by the mechanism 31 which moves the position of the rotary shaft 3a. The rotation center 3X in a viewpoint of CT scan may be coincident with the position of the rotary shaft. The rotary device 3a having the X-ray generator 1 and the X-ray detector 2 opposed to each other is rotated by a rotation angle β by the rotary mechanism around the rotary shaft 3a, while the center of the rotary mechanism or the rotary shaft 3a in correspondence to the rotation center moved is rotated relatively to the point 3X in the region of interest (in correspondence to the initial rotation center) according to the rotation angle β of the circular rotation, so that the relative positional relationship among the X-ray generator 1, the object O and the X-ray detector 2 are kept constant. FIGS. 2 and 3 show situations wherein the magnification is set smaller, but when the magnification is set larger, the point 3X in the region of interest is located nearer to the X-ray generator 1.

On the other hand, in a second X-ray CT scanner wherein an object is encircled according to a rotation angle of the rotation mechanism, a holder mechanism is provided for holding an object O between the X-ray generator 1 and the X-ray detector 2, and a movement mechanism, which will be explained later in detail, moves the holder mechanism in two-dimensional directions crossing the rotary shaft 3a in the rotary mechanism. FIG. 3 shows a situation of this control. Even when the position of the rotary shaft 3a is different from the point 3X in a region of interest in the object O, the distance between the point 3X in the region of interest and the X-ray generator 1 and the distance between the center 3X and the X-ray generator 1 are always kept constant due to the synthetic motion by synchronizing the rotation of the rotary device 3 with the rotary movement of the object with the movement mechanism 5 by a controller. That is, the rotation center 3X in a viewpoint of CT scan different from the rotary shaft 3a is set, and the rotary device 3 is rotated always around the point 3X in the region of interest in the object O.

The above-mentioned "rotation center 3X different from the rotary shaft 3a" means a rotation center in a viewpoint of CT scan defined independently of the mechanical rotary axis 3a, similarly to the case shown in FIG. 2, and it is realized by the mechanism for rotating the object. The rotation center 3X may be coincident with the position of the rotary shaft 3a (or the mechanical rotary axis). The rotary device is rotated by the rotary mechanism, while the point 3X in the region of interest in the object is rotated according to the rotation angle of the rotary device relatively to the rotation center of the rotary mechanism (the rotary shaft 3a) while the relative positional relationship among the X-ray generator 1, the object O and the X-ray detector 2 is kept constant.

The embodiments shown in FIGS. 2 and 3 are explained below in detail.

Figure 4A:
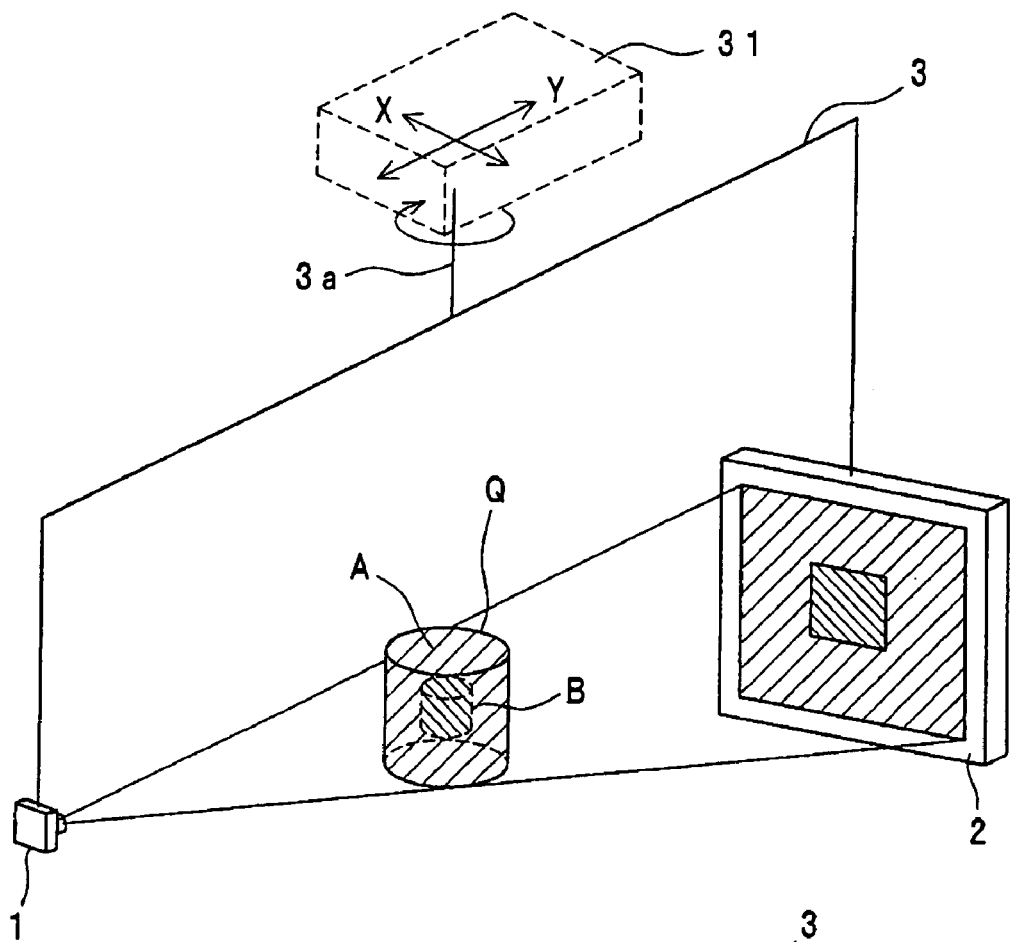
FIGS. 4A and 4B are schematic diagrams for a first X-ray CT scanner (a) and for a second X-ray CT scanner (b)

FIG. 4A shows the first X-ray CT scanner shown in FIG. 2 schematically. The rotary device 3 is a rotary arm in this embodiment having an X-ray detector 1 and an X-ray detector 2 opposing to each other while interposing an object O between them. By using the rotary arm, a rotary shaft 3a is set with a mechanically simple structure. The rotary device 3 is rotated around the rotary shaft 3a with a motor 33 for controlling the rotation. The rotary shaft 3a extends along the vertical direction. The rotary shaft 3a and the motor 33 are parts in the rotary mechanism. An XY table 31 is a mechanism for moving the rotary shaft 3a in two dimensions crossing the rotary shaft 3a or in a plane perpendicular to the rotary shaft 3a in this example. The XY table as a mechanism for moving the object has devices for moving an object in two crossing directions, and the moving of the object in two dimensions is controlled easily. The object O is fixed in the mechanism, and it has region B at and around the center and region A except region B.

Figure 4B:
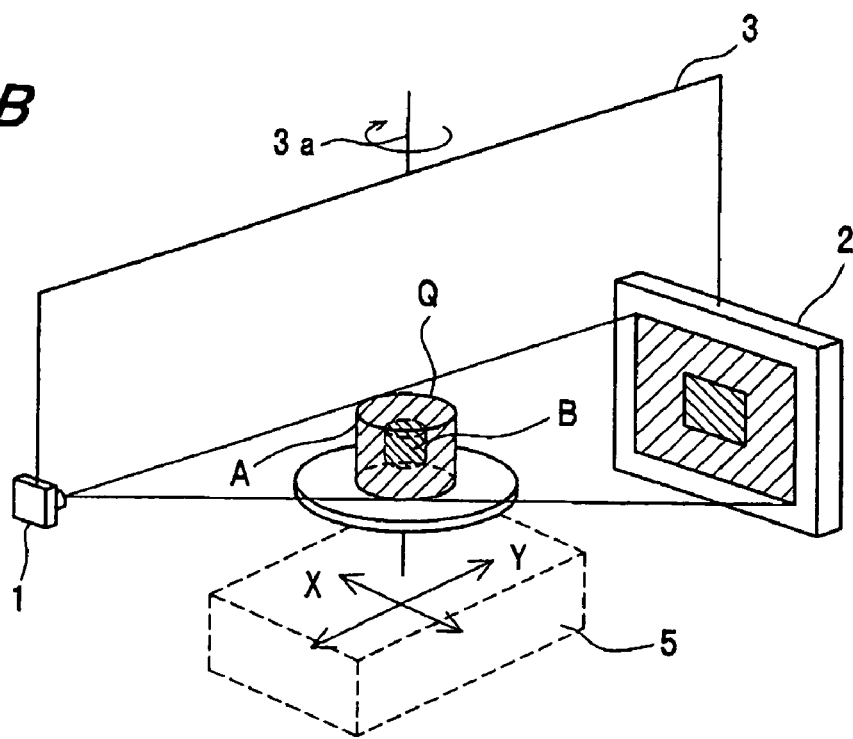

FIG. 4B shows the second X-ray CT scanner shown in FIG. 3 schematically. In this embodiment the rotary device 3 is a rotary arm having an X-ray detector 1 and an X-ray detector 2 opposing to each other while interposing an object O between them. The rotary device 3 is rotated around the rotary shaft 3a similarly to the example shown in FIG. 4A. The object O is fixed in the mechanism, and it has region B around the center and region A except region B. It is moved in to-and-fro, left-and-right and up-and-down directions with the device 5 (not shown) for moving the object. The device 5 is a mechanism for moving the object O in two dimensions crossing the rotary shaft 3a or in a plane perpendicular to the rotary shaft 3a in this example.

The mechanism for moving the rotary shaft shown in FIG. 4A is a mechanism for moving the rotary shaft 3a in two-dimensional directions crossing the rotary shaft 3a, while the mechanism for moving the object O shown in FIG. 4B is a mechanism for moving the object O in two-dimensional directions crossing the rotary shaft 3a. One of the two mechanisms may be provided so as to move one of the rotary shaft 3a and the object O. Alternatively, both of the two mechanisms may be provided for moving the rotary shaft 3a and the object O simultaneously.

FIGS. 5A and 5B show the embodiment shown in FIG. 4A in a plane. In the embodiment shown in FIG. 5A, the object O is imaged by moving the object O by distance α from the rotary shaft 3a towards the X-ray generator 1, while in the embodiment shown in FIG. 5B, the object O is imaged by moving the object O by distance α from the rotary shaft 3a towards the X-ray detector 2. The rotary device 3 is rotated by the above-mentioned mechanism, while the rotary shaft 3a is moved synchronously according to the rotation angle of the rotary device 3. According to the synthesized motion of the rotary device 3 and the rotary shaft 3a, the rotary axis 3a is rotated and moved relative to the point 3X in the region of interest, and the relative positional relationship among the X-ray generator 1, the object O and the X-ray detector 2 is kept constant. The rotary device 3 is rotated while the rotation center 3X in a viewpoint of CT scan different from the rotary shaft 3a in the rotation mechanism is always kept at the point 3X in the region of interest in the object.

In FIG. 5A, the rotary shaft 3a is rotated and moved along a circle with a radius a (or along positions LC1→LC2→LC3) relative to the point 3X in the region of interest separated by the distance α from the rotary shaft 3a towards the X-ray generator 1. The object O is moved from the X-ray detector 2 by distance α, and the X-ray detector 2 only detects the region B for reconstructing the region B. The region A is outside the detectable region. On the other hand, in FIG. 5B, the rotary shaft 3a is rotated and moved along a circle with radius a (or along positions LC1'→LC2'→LC3') relative to the point 3X in the region of interest separated by distance α from the rotary shaft 3a towards the X-ray detector 2. The object O is moved from the X-ray detector 2 by distance α, and the X-ray detector 2 detects not only the region B, but also the region A entirely. Thus, images of the regions A and B can be reconstructed. As can be understood with reference to FIGS. 5A and 5B, the magnification can be changed by changing the distance between the X-ray generator 1 and the rotation center 3X and/or the distance between the X-ray detector 2 and the rotation center 3X relatively to the distance between the X-ray generator 1 and the X-ray detector 2. Here, in FIGS. 5A and 5B, a rotation center 3X in the viewpoint of CT scan is set to the point 3X.

By moving only the rotary device without moving an object, it is possible to change the magnification for a scan from a value to another value. For example, at the start, the rotary shaft 3a is set to coincide with the point in the region of interest, and a scan is performed. Then, if it is desired to increase the magnification, the rotary shaft 3a is moved to the position LC1 shown in FIG. 5A, and a scan is performed wherein the rotary shaft 3a is rotated relative to the center 3X of the imaging region from the position LC1, along a circular orbit routing positions LC1, LC2 and LC3, as explained above. If it is desired to decrease the magnification, the rotary shaft 3a is moved to the position LC1' shown in FIG. 5B, and a scan is performed wherein the rotary shaft 3a is rotated relative to the center 3X of the imaging region from the position LC1', along a circular orbit routing positions LC1', LC2' and LC3', as explained above. Thus, the magnification for a scan can be changed freely without moving the object.

FIGS. 6A and 6B shows the examples shown in FIG. 4B as plan views. In FIG. 6A, the object O is moved from the rotary shaft of the rotary mechanism towards the X-ray generator 1 by distance α, while in FIG. 6B the object O is moved from the rotary shaft of the rotary mechanism towards the X-ray detector 2 by distance α. The rotary device 3 is rotated around the rotary shaft 3a, and the object O is moved synchronously according to the rotation angle by the mechanism 5 for moving the object O. According to the synthesized motion of the rotary device 3 and the object O, the relative positional relationship among the X-ray detector 1, the object and the X-ray generator 2 is kept constant. Thus, the rotary mechanism rotates the rotary device, while the rotation center 3X different from the rotary shaft 3a in the rotary mechanism is always located at the point 3X in the region of interest in the object.

In FIG. 6A, the point 3X in the region of interest far from the rotary shaft 3a by distance α towards the X-ray generator 1 is moved relative to the rotary shaft 3a along a circular orbit of radius a routing positions LC10, LC20 and LC30. The object is rotated by the mechanism 5 for moving the object, but the direction of the front of the object is not changed in a scan. For example, if the object is a human head, the head is rotated along the positions LC10, LC20 and LC30, while the head facing the same direction. The object O is moved by distance α in a direction to leave from the X-ray detector 2, and the X-ray detector 2 detects only the region B to reconstruct an image in the region B. The region A is outside the region detectable by the X-ray detector 2.

In FIG. 6B, the point 3X in the region of interest far from the rotary shaft 3a by distance α towards the X-ray detector 2 is moved relative to the rotary shaft 3a along a circular orbit of radius a routing positions LC10', LC20' and LC30'. The object O is moved by distance α towards the X-ray detector 2, and the X-ray detector 2 detects not only the region B but also the region A. Thus, an image of the two regions A and B can be reconstructed. Here, in FIGS. 6A and 6B, a rotation center 3X in the viewpoint of CT scan is set to the point 3X.

In the examples shown in FIGS. 6A and 6B, the rotation center 3X in a viewpoint of CT scan is controlled to be present always in the point 3X in the region of interest. That is, the first and second X-ray CT scanners have the rotary device 3 having the X-ray generator 1 and the X-ray detector 2 opposing to each other, the rotary mechanism for rotating the rotary device 3 around the rotary shaft 3a extending vertically to an X-ray beam generated by the X-ray generator 1, and the mechanism for moving the rotary shaft 3a and/or the object O in a plane perpendicular to the rotary shaft 3a. The mechanism for moving the rotary shaft 3a and/or the object O is the mechanism 3a for moving the rotary shaft in the first X-ray CT scanner or the mechanism 5 for moving the object in the second X-ray CT scanner. A controller to be explained later controls to set the rotation center 3X different from the rotary shaft 3a and to keep the distances of the X-ray generator 1 and the X-ray detector 2 relative to the point in the region of interest in the object O always constant, according to the synthesized and synchronized motion of the rotation of the rotary device 3 and the movement of the rotary shaft 3a and/or the object O.

Because the magnification can be changed easily as explained above, a user can set a magnification according to a purpose of a scan. For example, when a volume rendering image for an entire jaw of a person is needed for a dental X-ray CT scanner, the magnification is decreased to image a larger region. On the other hand, when a detailed image on a few teeth is needed, the magnification is decreased to image a smaller region in detail.

Figure 7B:
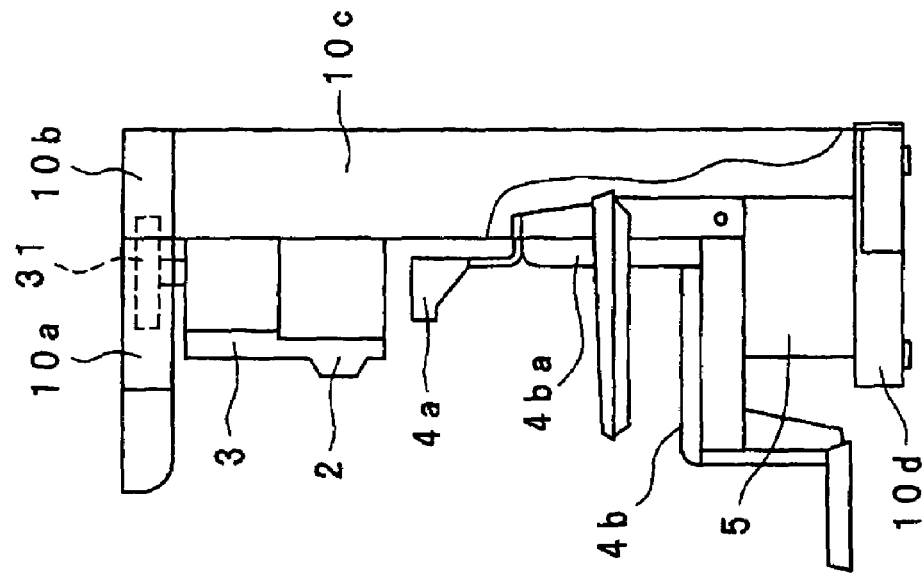
FIGS. 7A and 7B are diagrams of a basic structure of the first X-ray CT scanner.
Figure 7A:
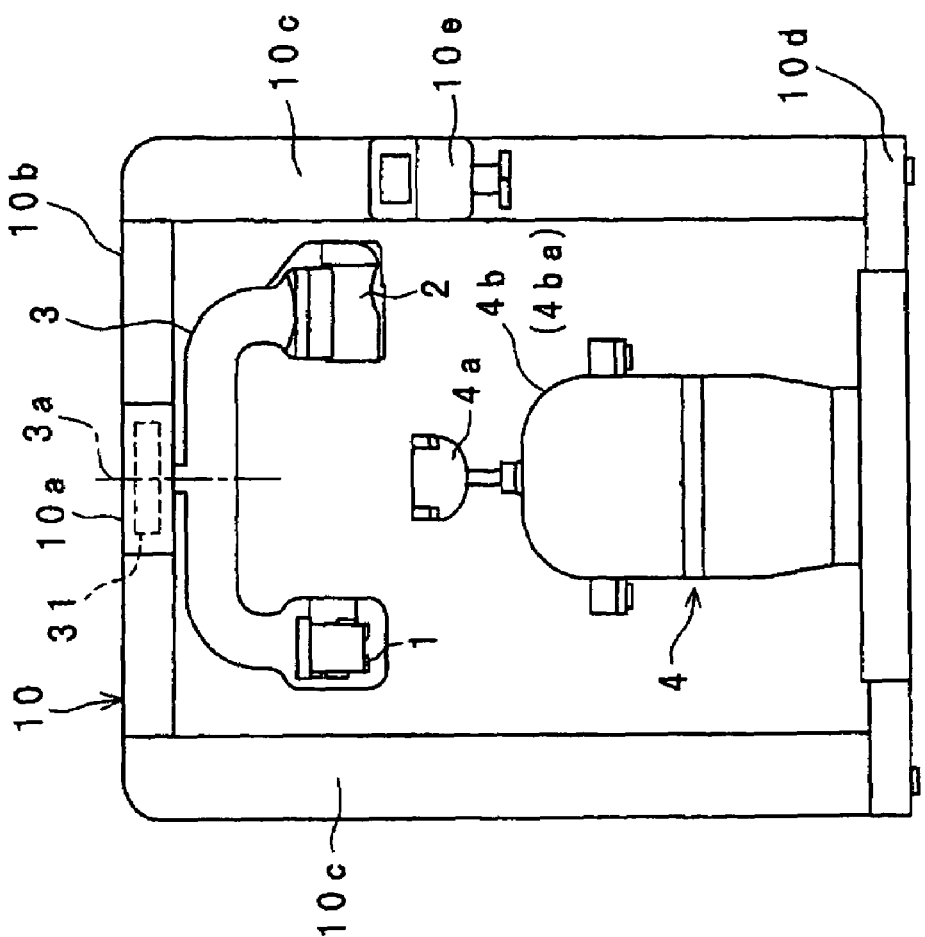
Figure 8:
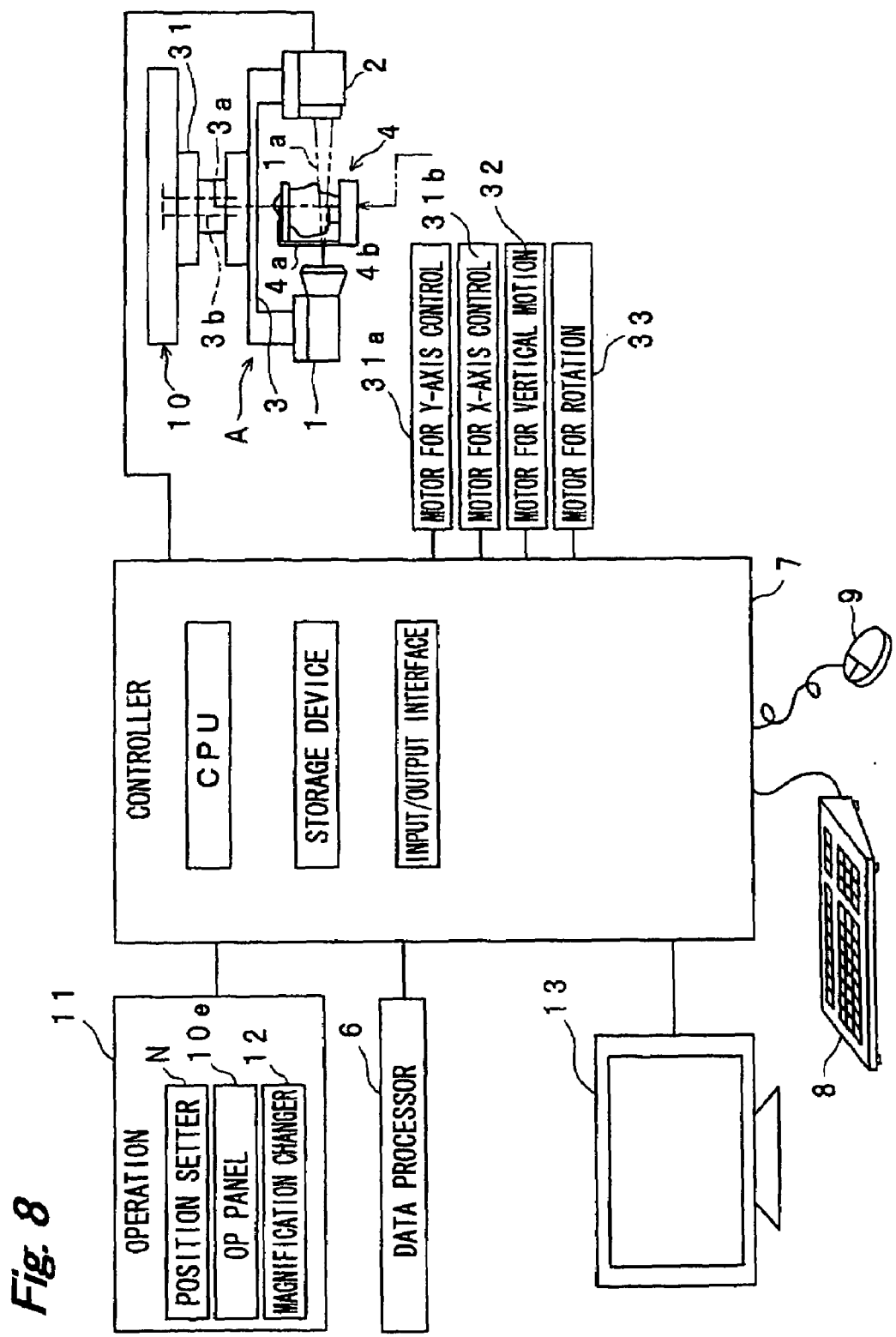
FIG. 8 is a diagram of a controller system of the first X-ray CT scanner.

Next, an example of the first X-ray CT scanner is explained in detail. FIGS. 7 and 8 show an example of the first X-ray CT scanner shown in FIGS. 2, 4A, and 5A and 5B. A main frame 10 has a gate-type very hard structure which supports the entire scanner. The main frame 10 consists of a top frame 10a for supporting the rotary arm 3 rotatably, a pair of lateral beams 10b for holding the ends of the top frame 10a, a pair of vertical beams 10c supporting the lateral beams 10b, and a base 10d for mounting the vertical beams 10c as a base for the entire scanner. The mechanism 5 for moving the object is mounted on the base 10d, and it has a chair 4b as a device 4 for holding the object. An operation panel 10e is provided on one of the vertical beams 10c.

The rotary device 3 is a U-like rotary arm with the X-ray generator for emitting an X-ray corn beam and an X-ray detector 2 (a two-dimensional X-ray image sensor) opposing to each other. In a CT scan, while the rotary device 3 is rotated around an object, the object is exposed to the X-ray corn beam, and the X-rays transmitting the object are detected with the X-ray detector 2 as projection data. A three-dimensional image of the object is reconstructed from the projection data.

The XY table 31 is fixed on the top frame 10a, supporting the rotary device 3 rotatably. The XY table 41 is an example of the mechanism for moving the rotary shaft 3a extending vertically in a plane perpendicular to the rotary shaft 3a. As will be explained later, the XY table 31 can be moved in a horizontal plane in directions perpendicular to each other. The XY table 31 has a Y table for movement in Y direction as a first direction and an X table supported by the Y table for movement in X direction as a second direction perpendicular to Y direction. (X direction is the left-and-right direction in FIG. 7A, and Y direction is a direction perpendicular to X direction.) Further, a motor 31a for moving the XY table 31 in X direction, a motor 31b for moving the XY table 31 in Y direction, a motor 32 for moving the rotary device in a direction perpendicular to the XY table 31 (up-and-down direction in FIG. 7A), and a motor 33 for rotating the rotary device 3 are provided for the XY table. The motor 33 rotates the rotary shaft (rotation center) 3a provided in a cavity 3b in the rotary device 3. By controlling the motors 31a and 31b for the movements in X-axis and in Y-axis, the rotary shaft 3a of the rotary device 3 can be moved up and down, and by driving the motor 32, the rotary device 3 can be moved up and down. When an object is scanned, the motor 33 is driven at a constant speed to rotate the rotary device 3 around the object. In this example, the XY table 31 is used to move the rotary shaft 3a in the first direction (for example, X direction) different from the rotary axis and in the second direction (for example, Y direction) perpendicular to the first direction. In general, the second direction may not be perpendicular to the first direction, or the rotary shaft 3a is moved in the first direction and in the second direction different from the first direction. Further, in this example, the rotary shaft 3a extends vertically. However, the rotary shaft 3a may extend in a horizontal direction. For example, a patient lying in a horizontal direction can be imaged.

Figure 9:
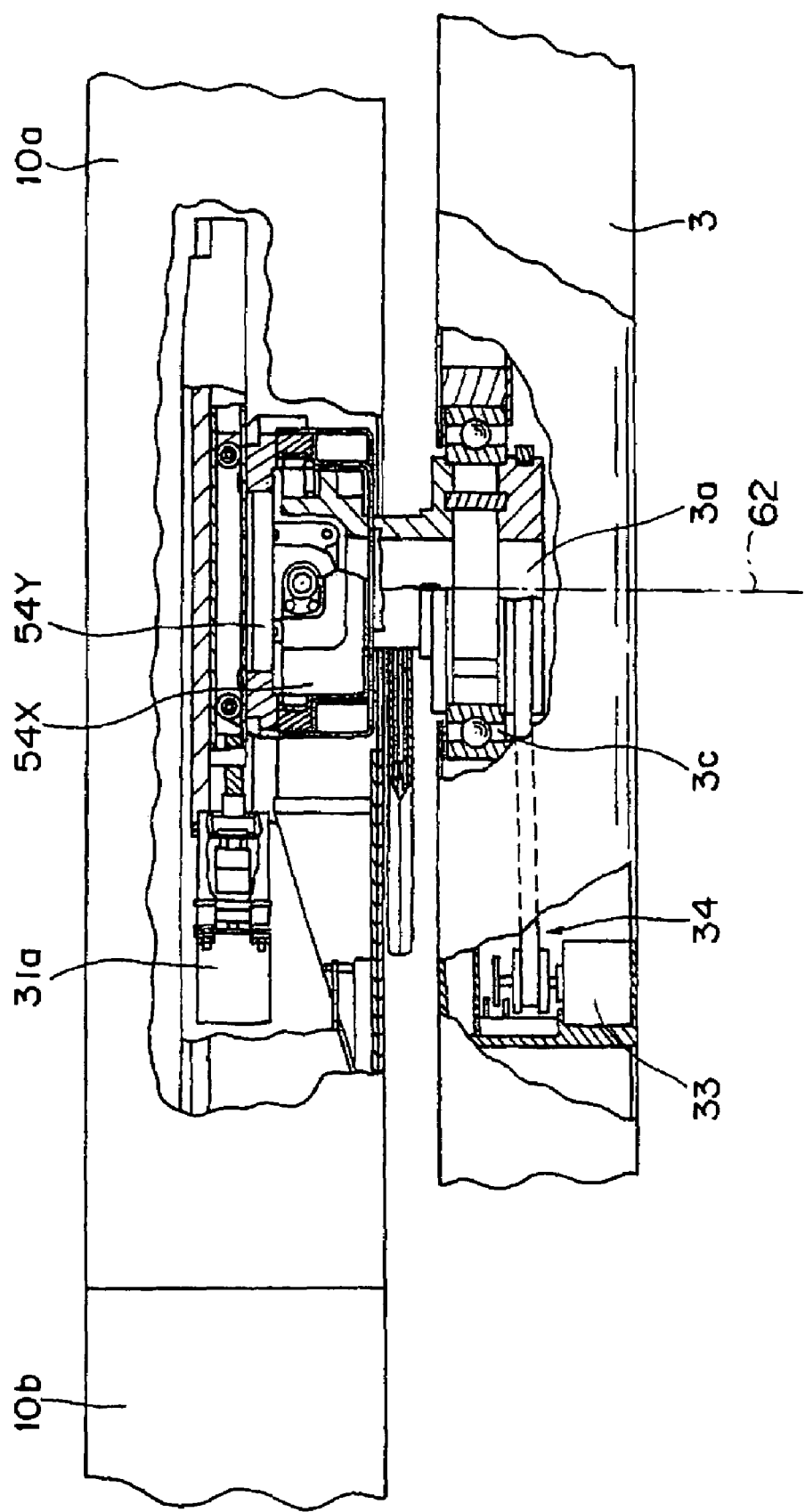
FIG. 9 is a diagram of a rotation system of the first X-ray CT scanner.

FIG. 9 shows a part in the CT scanner for the control of the position of the rotary arm 3 and the rotation. The top frame 10a has the table 54Y (Y table) for moving in to-and-fro direction (Y direction), the other table 54X (X table) supported by the table 54Y for moving in lateral direction (X direction), the Y-axis control motor 31a for moving the Y table in Y direction, the X-axis control motor 31b (not shown) for moving the X table in X direction, and the motor 33 for rotating the rotary arm 3 around a vertically-extending rotary axis 62 of the rotary shaft 3a which connects the X table 54X with the rotary arm 3. The rotary arm 3 has a bearing 3c. The motor 33 is mounted inside the rotary arm 3, and it drives the bearing 3c with a belt 34 so as to rotate the rotary shaft 3a. The rotary shaft 3a, the bearing 3c, the belt 34 and the motor 33 are components of an example of the rotary mechanism for rotating the rotary device 3. By driving the three motors according to a predetermined program, the XY table can be moved in to-and-fro direction (Y direction) and in left-and-right direction (X direction) while the rotary arm 3 is rotated.

Figure 10:
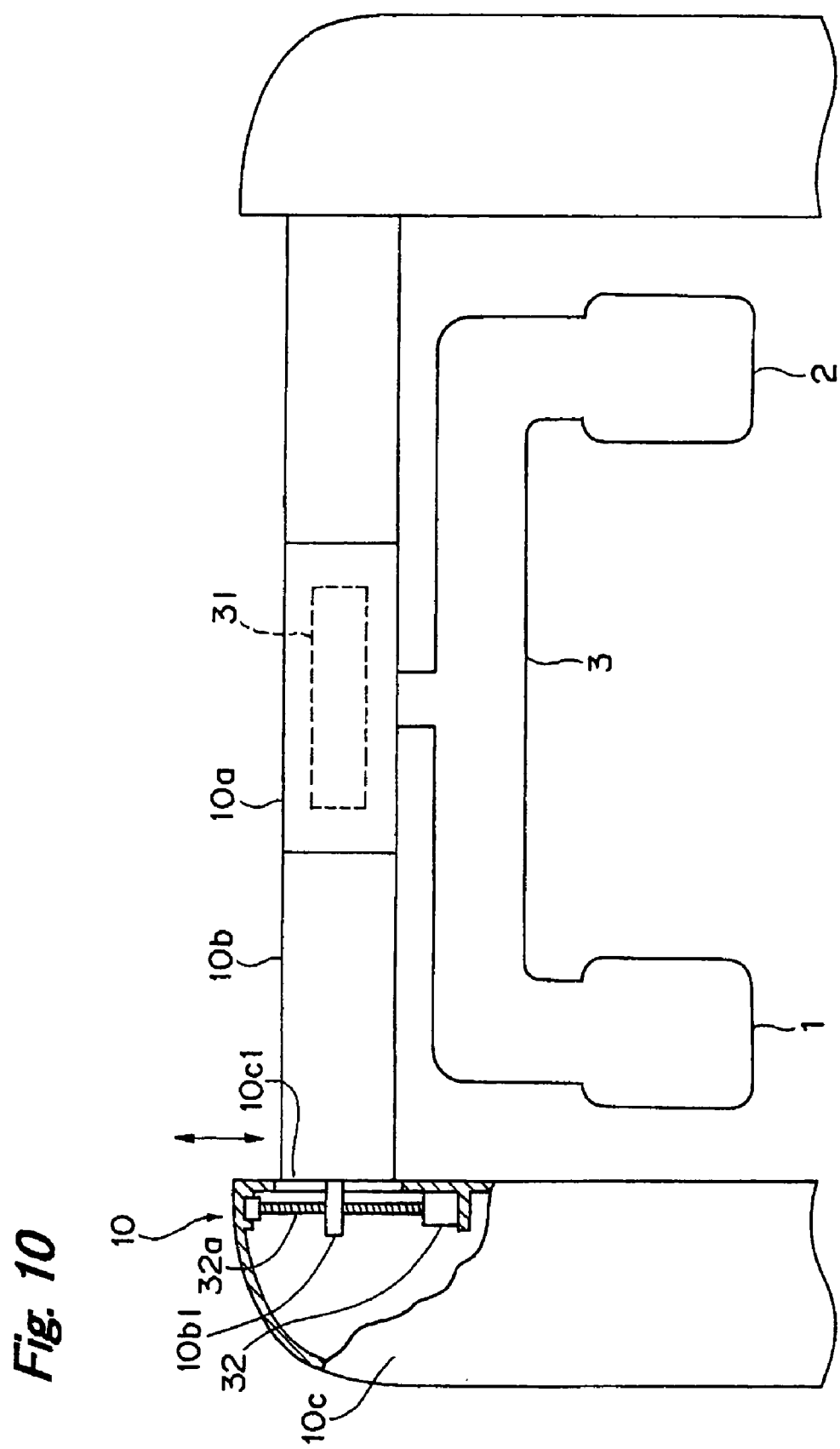
FIG. 10 is a diagram of a part related to the up-and-down control of the rotary arm.

FIG. 10 shows an example of a part of the CT scanner related to the up-and-down control of the rotary arm 3. The lateral beam 10b can be moved up and down relative to the vertical beam 10c. A protrusion 10b1 extends from an end of the lateral beam 10b and penetrates a hole 10c1 in the vertical beam 10c. The protrusion 10b1 has a threaded hole (not shown), and a threaded shaft 32a of the motor fixed to the vertical beam 10c is engaged with the threaded hole of the protrusion 10b1. The threaded shaft 32a is extended in a direction perpendicular to the X and Y directions. The protrusion 10b1, the hole 10c1, the threaded hole, the motor 32 and the threaded shaft 32a are provided for the two ends of the lateral beam 10a and for the vertical beams 10c. The threaded shaft 32a is rotated by the motor 32 to move the protrusion 10b1 up or down. Thus the entire lateral beam 10b is moved up or down so that the rotary arm 3 is also moved up or down.

Figure 11:
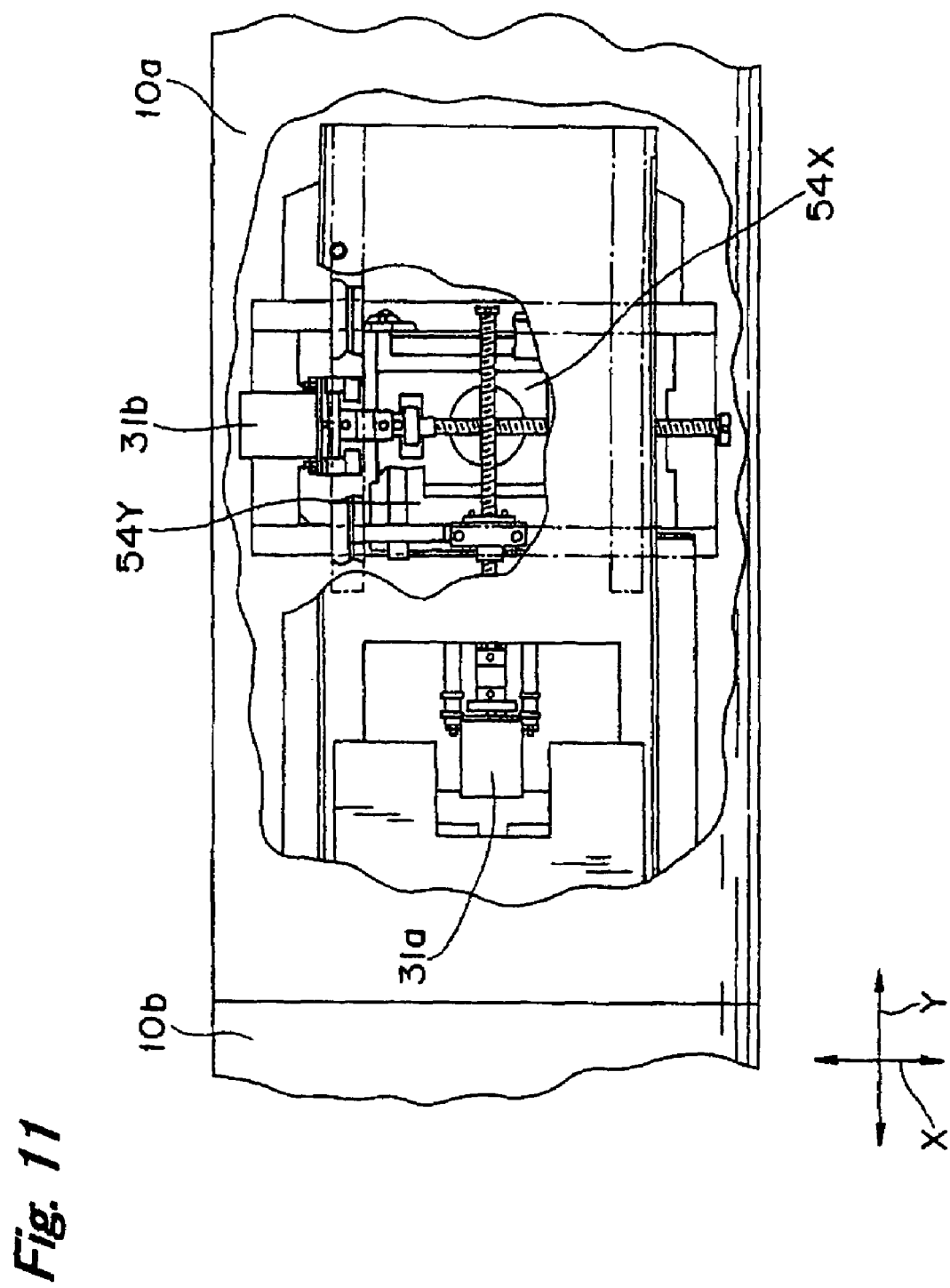
FIG. 11 is a diagram of a part related to the control of the position of the rotary arm and the rotation.

FIG. 11 shows a part of the CT scanner for the control on the position of the rotary arm 3 and the rotation as a plan view, having the table 54Y (Y table) for to-and-fro direction, the table 54X (X table) supported by the table 54Y for a lateral direction, the motor 31a for moving the Y table in Y direction and the motor 31b for moving the X table in X direction. The table 54X is an example of a first moving device which moves the rotary shaft 3a in a first direction, and the table 54Y is an example of a second moving device which moves the rotary shaft 3a in a second direction different from the first direction. In the above-mentioned example, X direction is perpendicular to Y direction for the convenience of the calculation of coordinates. However, the first and second directions may cross at an arbitrary angle as far as the two dimensional control is possible.

Figure 12:
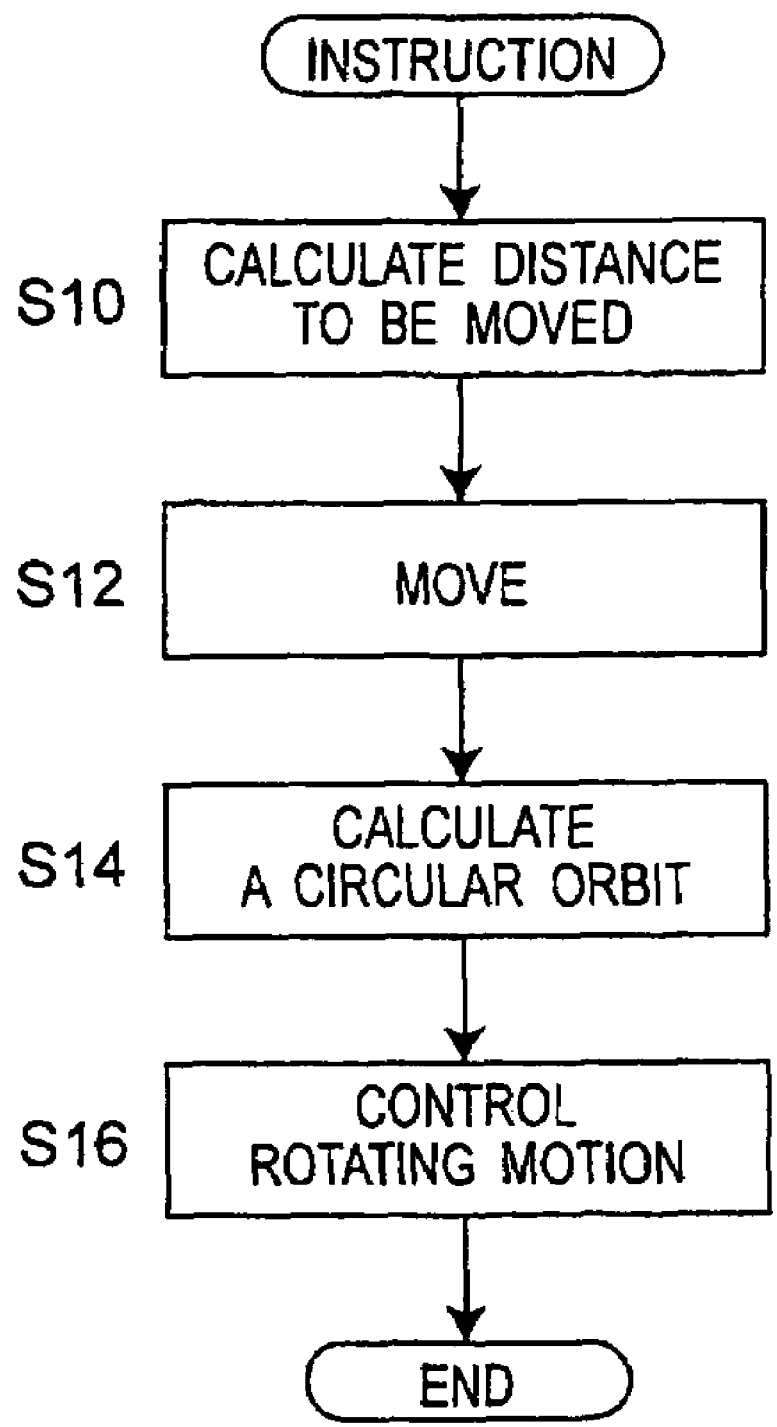
FIG. 12 is a flowchart of rotation control.

Next, rotation control by the controller 7 is explained for changing a magnification in the CT scan control. A case is explained where the rotation center is moved along a circular orbit. First an operator sets a magnification with the magnification changer 12 provided in the operation device 11, and the control as shown in FIG. 12 is evoked. First, the distance to be moved of the rotation center is calculated according to the magnification (S10), and the motors 31b and 31a for movement in X axis and in Y axis are activated to move the rotary shaft 3a by the calculated distance (S12). Further, the circular orbit of the rotation center is calculated (S14). In a CT scan, the motor 33 for rotating the rotary arm 3 is activated, while the motors 31b and 31a are activated to move the rotary shaft 3a along a circle with radius a having its center at an object (S16). That is, in the CT scan control, the rotation conditions of the motor 33 for rotation and the orbit of movement of the motors 31b and 31a in X and Y directions are calculated according to the magnification, and the motors 33, 31b and 31a are controlled according to the rotation conditions and the calculated orbit. Thus, according to the synthesized movement due to the rotation and the movement, the rotary arm 3 is rotated by setting the point in the region of interest in the object O as the rotation center 3X in a viewpoint of CT scan different from the rotary shaft 3a.

Figure 13:
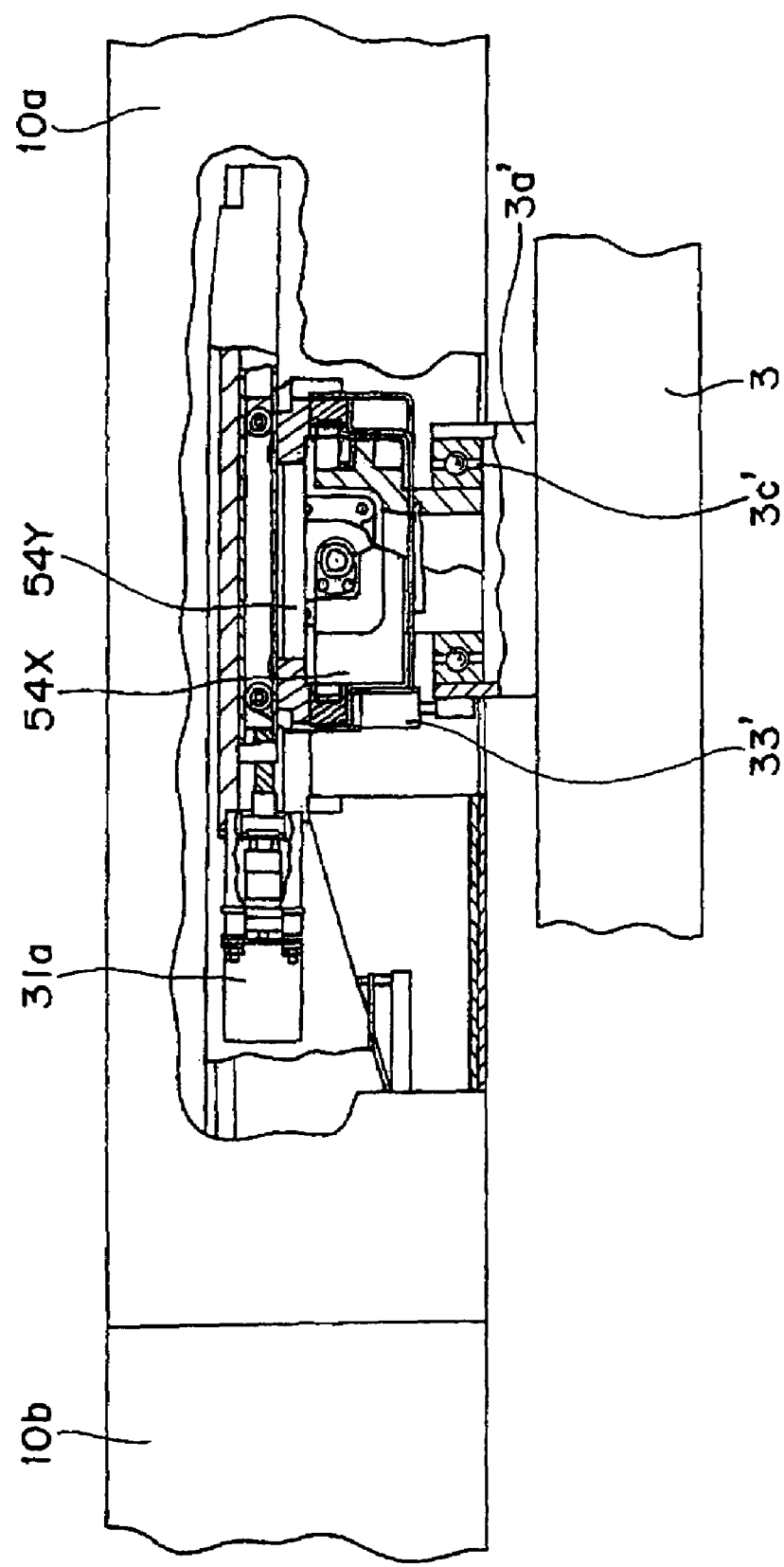
FIG. 13 is a diagram of a modified example of a rotation system.

In the example shown in FIG. 9, the motor 33 for controlling the rotation is arranged in the rotary arm 3. However, as shown in FIG. 13, a motor 33' for controlling the rotation may be provided in the same housing as the top frame 10a. In the example shown in FIG. 13, the motor 33 is not provided in the rotary arm 2, in contrast to the example shown in FIG. 9, and the motor 33' is mounted on a table 54X (X table) in a housing of the top frame 10a. A rotary shaft 3a' of the rotary arm 3 supported rotatably with a bearing 3c' with the table 54X is driven by the motor 33'. Because the XY table (or a mechanism for moving the rotary shaft) is provided in the same housing as the motor 33' for controlling the rotation (or a rotary mechanism), a rotary mechanism can be set in a space rather wide two-dimensionally for the mechanism for moving the rotary shaft. Further, because they are set in the same housing, the rotary mechanism is not needed to be provided in the rotary device, and the structure of the rotary device can be simplified.

When the position of the rotation center is changed in order to change the magnification as explained above, for example, when an object is moved relatively by distance $\alpha$ (>0) towards the X-ray detector 2, the motors 31b and 31a are activated to move the X table 54X and the Y table 54Y by distance $\alpha$ to make the X-ray detector 2 nearer to the object O. In a CT scan, the motor 33 is activated to rotate the rotary arm 3, while the motors 31b and 31a are activated to move the rotary shaft 3a around the object along a circular orbit with radius $\alpha$. The principle of scan is explained above with reference to FIG. 5.

Figure 14:
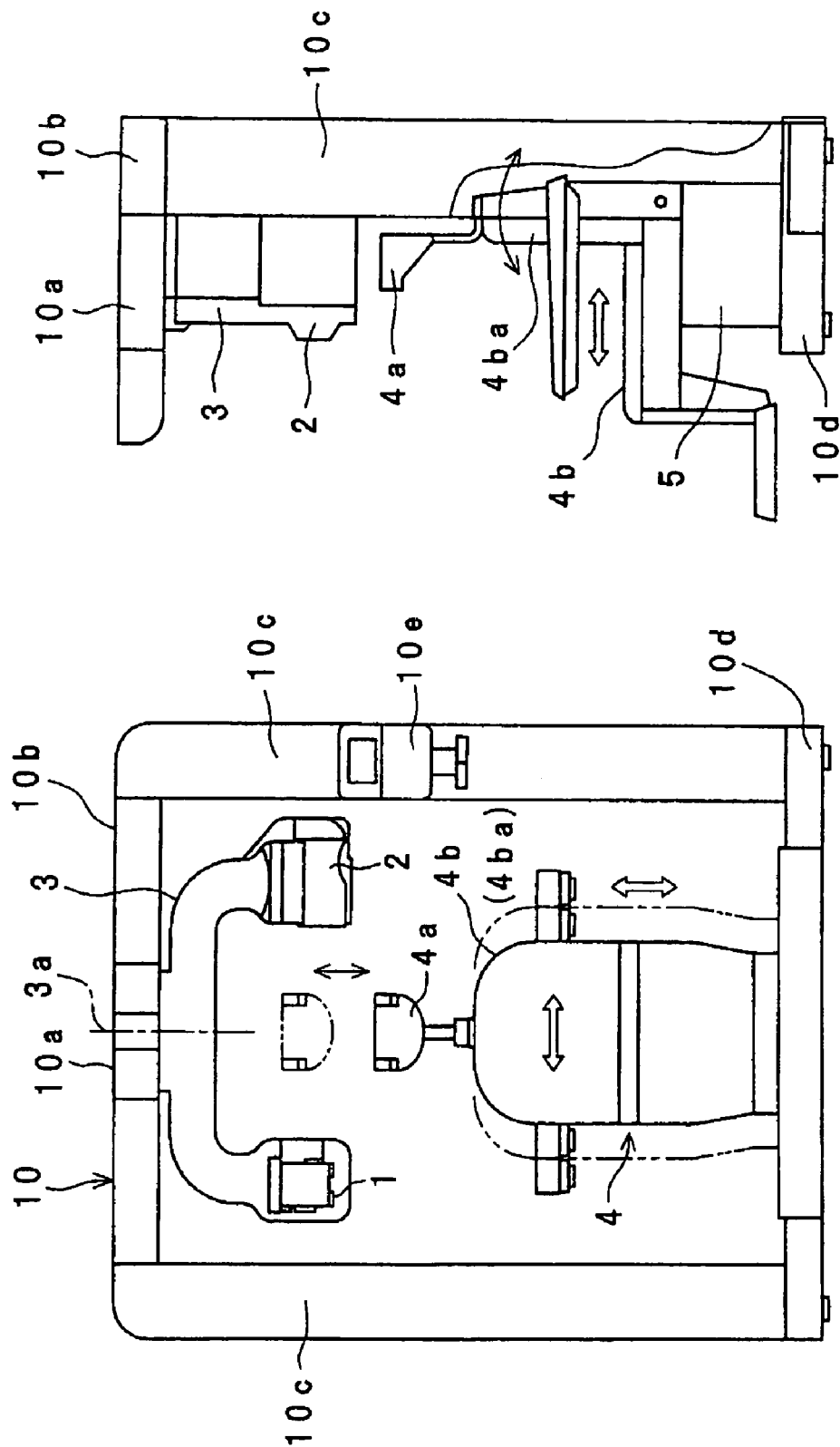
FIGS. 14A and 14B are diagrams of a basic structure of the second X-ray CT scanner.
Figure 15:
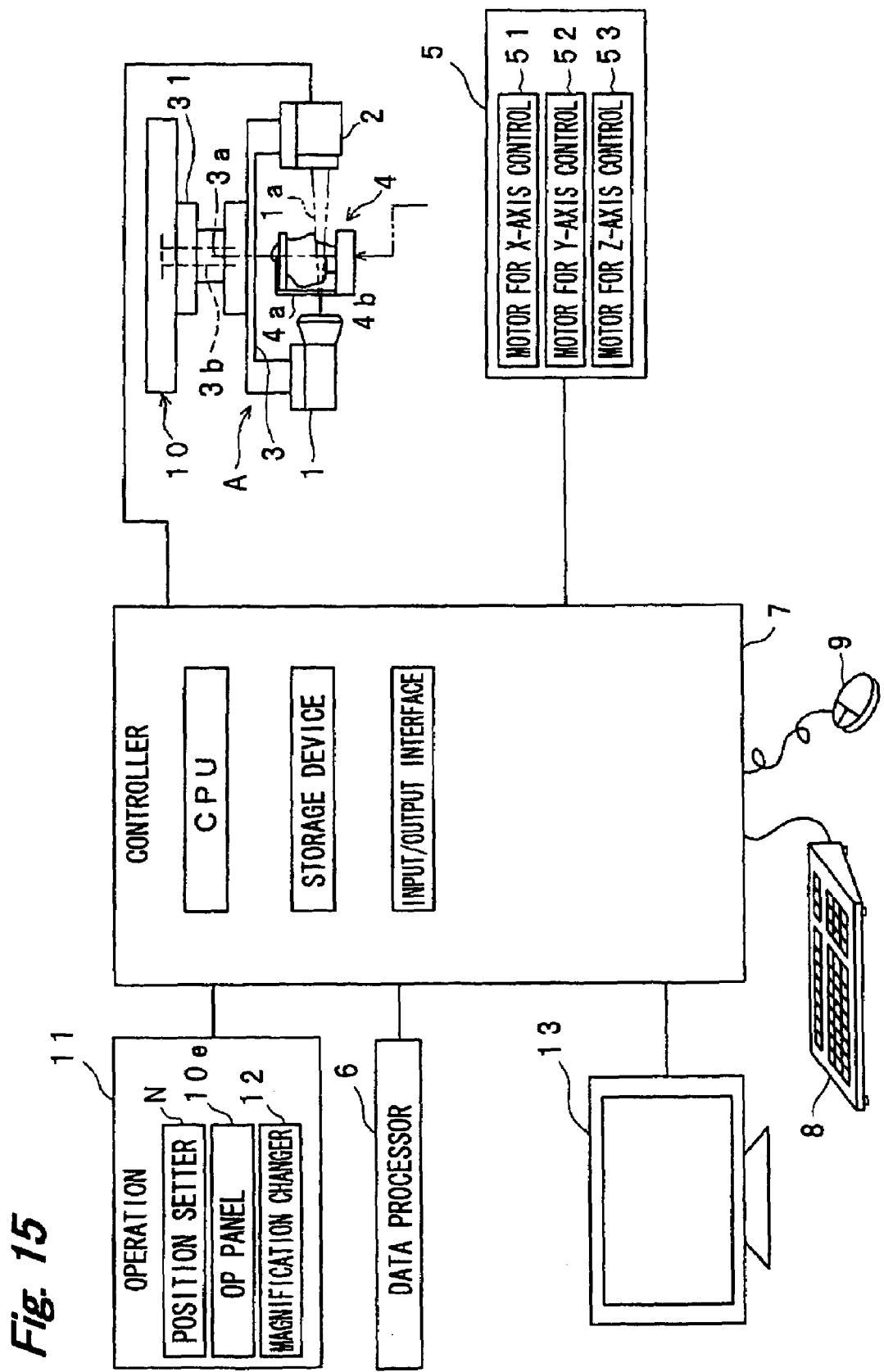
FIG. 15 is a diagram of a controller system of the second X-ray CT scanner.

Next, an example of the second X-ray CT scanner is explained in detail. FIGS. 14 and 15 show an example of the second X-ray CT scanner shown in FIGS. 3, 4B, 6A and 6B. Its basic structure is similar to that of the first X-ray CT scanner shown in FIGS. 7 and 8, except that the device 5 for moving the object in X and Y directions is used instead of the XY table as the mechanism for moving the rotary shaft. The device 5 for moving the object is set on the base 10d of the main frame 10, and a chair 4b is mounted thereon to hold the object (or a patient) in a sitting posture. A mechanism 4 for holding the object has the chair 4b and a head fixing device 4a provided at the back of the chair 4b. The mechanism 4 for holding the object is not limited to the above-mentioned chair 4b and the head fixing device 4a. For example, it may be any device for holding an object such as a chin rest for setting the object's chin or ear rods for fixing ears' positions of the patient. The device for moving the object's position can move the chair 4b in X, Y and Z directions, or in to-and-fro direction, in left-and-right direction and in up-and-down direction. The device for moving the object's position in X direction is the first moving device, and the device for moving the object's position in Y direction is the second moving device.

The device 5 for moving the object has a motor 51 for moving the chair 4b in X direction, a motor 52 for moving the chair 4b in Y direction, and a motor 53 for moving the chair 4b in Z direction as a device for movement in up-and-down direction. The movement of tables in X-, Y- and Z-axes with the motors 51, 52 and 53 may be realized with use of a rack and pinion, a ball screw or a conventional thread. It is desirable that the positioning is precise. The device 5 for moving the object is an example of the mechanism for moving the object in a plane perpendicularly to the rotary shaft 3a of the rotary mechanism explained above with reference to FIG. 4B. In this embodiment, the mechanism 5 for moving the object moves the chair 4b in a first direction (for example, X direction) and in a second direction perpendicular to the first direction (for example, Y direction). However, the chair 4b may be moved in a second direction, not perpendicular to, but different from the first direction.

When the position of an object O is changed in order to set a magnification as explained above, for example, when the object O is moved relatively by the distance $\alpha$ (>0) towards the X-ray detector 2, the motors 51 and 52 are activated to move the chair 4b by the distances in X and Y directions in correspondence to distance $\alpha$ to make the object O nearer to the X-ray detector 2. In a CT scan, the motor 33 is activated to rotate the rotary arm 3, while the motors 31b and 31a are activated to move the rotary shaft 3a around the object along a circular orbit with radius $\alpha$. The principle of scan is explained above with reference to FIGS. 6A and 6B.

Next, CT scan control of the X-ray CT scanner is explained. As shown in FIG. 8, the X-ray CT scanner 20 as an example of the first X-ray CT scanner has the controller 7 including a computer. The controller 7 has the computer including a central processing unit (CPU), a storage device and an input/output interface, and it is connected to a data processor including a coprocessor, a keyboard 8, a mouse 9, a display monitor 10 such as a liquid crystal display, and an operation device including an operation panel 10e. The operation device 7 includes a magnification changer 12 for an operator to set a magnification value. The controller 7 is also connected to the X-ray generator 1 and the X-ray detector 2, and controls the motors 31a, 31b, 32 and 33. The storage device includes a control program for a CT scan and a processing program for calculating a three-dimensional CT data from the projection data.

As shown in FIG. 15, the X-ray CT scanner 20 as an example of the second X-ray CT scanner has a controller 7 including a computer. The controller 7 has the computer including a central processing unit (CPU), a storage device and an input/output interface, and it is connected to a data processor including a coprocessor, a keyboard 8, a mouse 9, a display monitor 10 such as a liquid crystal display, and an operation device including an operation panel 10e. The operation device 7 includes a magnification changer 12 for an operator to set the magnification. The controller 7 is connected to the X-ray generator 1 and the X-ray detector 2, and it controls to drive the motors 51, 52 and 53 for moving the object's position. The storage device includes a control program for a CT scan and a processing program for calculating a three-dimensional CT data from the projection data. As shown in FIG. 15, the second X-ray CT scanner may have an XY table 31 used in the above-mentioned first X-ray CT scanner.

When the object is moved along a circular orbit in the second X-ray CT scanner shown in FIGS. 14 and 15, the rotation control for changing the magnification is similar to the counterpart in the first X-ray CT scanner explained above with reference to FIG. 12. However, because the chair is moved in the second X-ray CT scanner whereas the rotary shaft is moved in the first X-ray CT scanner, the rotation control is different in this point. At step S10 the distance for the chair 4b to be moved is calculated, and the orbit is calculated according to the magnification, and at step S12 the motors 51 and 52 are activated to move the chair 4b by the calculated distance. Further, at step S14 the circular orbit of the chair 4b is calculated. In a CT scan, at step S16, the motor 33 is activated to rotate the rotary arm 3, while the motors 51 and 52 are activated to move the chair 4e around the rotation center along a circle of radius $\alpha$.

Figure 16:
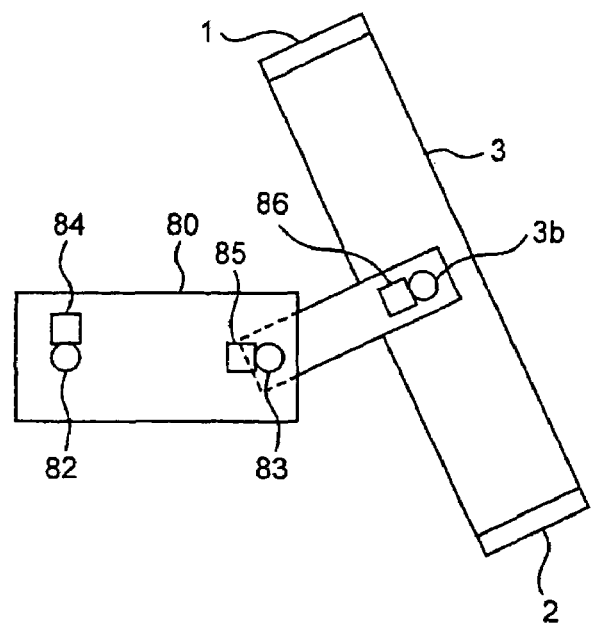
FIG. 16 is a diagram of a modified example of the two-dimensional movement mechanism.

In the above-mentioned first X-ray CT scanner, the XY table 31 is used as the mechanism for moving the rotary shaft 3a in a plane perpendicular to the rotary shaft 3a. For example, as shown in FIG. 16 schematically, a position of the rotary arm may be changed by using link members connected to each other rotatably. In an example shown in FIG. 16, two link members 80 and 81 are connected in series. The first link member 80 is connected to the top shaft 10a with a shaft 82 rotatably, and the second link member 81 is connected rotatably to the first link member 80 with a shaft 83. Further, the second link member 81 is connected rotatably to a bearing of the rotary shaft 3a. The shafts 82, 83 and the rotary shaft 3a are moved with the motors 84, 85 and 86. The controller 7 controls the motors 84, 85 and 86 to move the position of the rotary shaft 3a in a two-dimensional plane perpendicular to the rotary shaft 3a.

Figure 17:
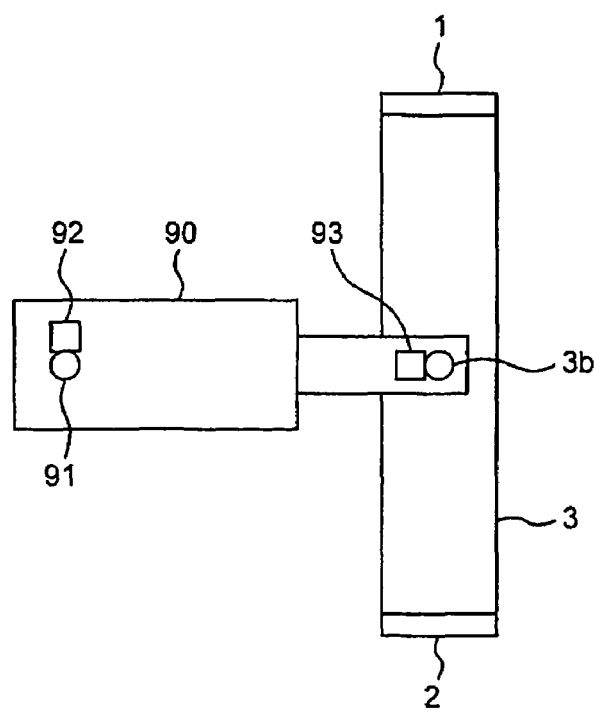
FIG. 17 is a diagram of another modified example of the two-dimensional movement mechanism.

FIG. 17 shows another modified example of the mechanism for moving the rotary shaft. In this example, an extensible member 90 as a link device is used. One end of the extensible member 90 is connected rotatably with a shaft 91 to the top frame 10a, while the other end thereof is connected rotatably to a bearing of the rotary shaft 3a of the rotary arm 3. The extensible member 90 and the rotary shaft 3a are moved with motors 92 and 93 for driving them. The controller 7 controls the extensible member 90 and the motors 92, 93 to move the position of the rotary shaft 3a in a two-dimensional plane perpendicular to the rotary shaft 3a. Because the mechanisms for moving the rotary shaft as shown in FIGS. 16 and 17 are constructed with one or more connection members connected in series, the movement of the rotary shaft in a two-dimensional plane can be controlled with a simple structure.

In the above-mentioned embodiments, an X-ray CT scanner has one of a mechanism for moving the rotary shaft or a mechanism for moving an object. However, if an X-ray CT scanner has both of the mechanism for moving the rotary shaft and the mechanism for moving an object, as mentioned above with reference to FIG. 15, the rotation can be controlled by using a various combination of the two mechanisms. In this case, it is possible to select one of the mechanism for moving the rotary shaft and the mechanism for moving an object. It is also possible to use the two mechanisms simultaneously so that the rotation center in viewpoint of CT scan different from the mechanical rotary axis is always kept at the point in the region of interest in an object. Thus, the magnification can be changed according to the distance between the X-ray generator and the rotation center and/or the distance between the X-ray detector and the rotation center, relative to the distance between the X-ray generator and the rotation center.

Examples of various patterns for the movement of the rotary shaft or the object are listed below.

(a) Control in all the X, Y and Z directions with use of the mechanism for moving the rotary axis.

(b) Control in all the X, Y and Z directions with use of the mechanism for moving an object.

(c) Control in all the X and Y directions with use of the mechanism for moving the rotary axis, and control in the Z directions with use of the mechanism for moving an object.

(d) Control in the X and Y directions with use of the mechanism for moving an object, and control in the Z directions with use of the mechanism for moving the rotary axis.

(e) Control in the X and Y directions with use of both of the mechanism for moving the rotary axis and the mechanism for moving an object.

(f) Control in all the X, Y and Z directions with use of both of the mechanism for moving the rotary axis and the mechanism for moving an object.

By using the patterns (e) and (f), it is advantageous to decrease the displacements of both of the rotary device and the mechanism for holding the object smaller.

The magnification can be changed in the above-mentioned embodiments. However, needless to say, even when the magnification is fixed or it cannot be changed, an X-ray CT scan is possible by changing the position of the rotary shaft of the rotary mechanism and the position of the rotation center in a viewpoint of CT scan and by rotating the rotary device always around the point in the region of interest in an object as the rotation center different from the rotary shaft of the rotary mechanism, according to the synthesis of the rotation of the rotary device 3 and the movement of the rotary shaft 3a and/or the object O.

The rotary device 4 may be the above-mentioned U-like rotary arm, but it may also be a known gantry used for a scan for a patient lying on a bed. Further, any structure which can rotate an X-ray generator and an X-ray detector opposing each other may be used.

The applicant of this invention already disclosed a radiography apparatus which can be used both for CT mode and panorama mode, as disclosed in Japanese patent laid open Publication H10-225455/1998. It is possible to add the radiography apparatus to the structure of this invention. Thus, a panoramic tomography image can be acquired in the X-ray CT scanner according to the invention.

Though this invention can be applied to a dental X-ray CT scanner, it can also be applied to an X-ray CT scanner for otolaryngology wherein the object is, for example, a very small part such as stapes or a large part of a head.

Although embodiments have been disclosed and described, it is apparent that other embodiments and modification of the invention are possible.

The invention claimed is:

1. An X-ray CT scanner comprising:
   a rotary device comprising an X-ray generator and an X-ray detector opposing to each other, to be provided for interposing an object between them;
   a rotary mechanism for rotating the rotary device around a rotary axis;
   a mechanism for moving the rotary axis of the rotary mechanism in a two-dimensional direction crossing the rotary axis; and
   a controller which controls the rotary mechanism and the mechanism for moving the rotary axis, wherein rotation of the rotary device by the rotary mechanism and movement of the rotary axis by the mechanism for moving the rotary axis are synchronized so as to set a rotation center of a synthesized motion of the rotation of the rotary device and the movement of the rotary axis at a point in a region of interest during a CT scan, the rotation center being different from and defined independently of the rotary axis;
   whereby a magnification is changed by setting a distance between the X-ray generator and the rotation center and/or a distance between the X-ray generator and the rotation center.

2. The X-ray CT scanner according to claim 1, wherein the mechanism for moving the rotary axis comprises:
   a first moving device which moves the rotary axis of the rotary mechanism in a first direction; and
   a second moving device which moves the rotary axis in a second direction different from the first direction.

3. The X-ray CT scanner according to claim 1, wherein the mechanism for moving the rotary axis and the rotary device are mounted in the same housing.

4. The X-ray CT scanner according to claim 1, wherein the mechanism for moving the rotary axis comprises a link member or a plurality of link members connected in series connected to a bearing of the rotary mechanism, whereby the rotation center can be moved in a two-dimensional direction crossing the rotary axis.

5. The X-ray CT scanner according to claim 1, wherein the rotary axis of the rotary mechanism extends vertically.

6. The X-ray CT scanner according to claim 1, wherein the rotary device is comprised of rotary arm.

7. An X-ray CT scanner comprising:
a rotary device comprising an X-ray generator and an X-ray detector opposing to each other, to be provided for interposing an object between them;
a rotary mechanism for rotating the rotary device around a rotary axis;
a mechanism for moving the object around the rotary axis in two-dimensional directions crossing the rotary axis; and
a controller which controls the rotary mechanism and the mechanism for moving the object, wherein rotation of the rotary device by the rotary mechanism and movement of the object by the mechanism for moving the object are synchronized so as to set a rotation center of a synthesized motion of the rotation of the rotary device and the movement of the object at a point in a region of interest during a CT scan, the rotation center being different from and defined independently of the rotary axis;
whereby a magnification is changed by setting a distance between the X-ray generator and the rotation center and/or a distance between the X-ray detector and the rotation center.

8. The X-ray CT scanner according to claim 7, wherein the mechanism for moving the object comprises:
a first moving device which moves the object in a first direction; and
a second moving device which moves the object in a second direction different from the first direction.

9. The X-ray CT scanner according to claim 7, wherein the rotary axis of the rotary mechanism extends vertically.

10. The X-ray CT scanner according to claim 7, wherein the rotary device is comprised of rotary arm.

11. An X-ray CT scanner comprising:
a rotary device comprising an X-ray generator and an X-ray detector opposing to each other, to be provided for interposing an object between them;
a rotary mechanism for rotating the rotary device around a rotary axis;
a mechanism for moving the rotary axis of the rotary mechanism and/or the object in two-dimensional directions crossing the rotary axis; and
a controller which controls the rotary mechanism and the mechanism for moving the rotary axis and/or the object, wherein rotation of the rotary device by the rotary mechanism and movement of the rotary axis and/or the object by the mechanism for moving the rotary axis and/or the object are synchronized so as to set a rotation center of a synthesized motion of the rotation of the rotary device and the movement of the rotary axis and/or the object at a point in a region of interest during a CT scan, the rotation center being different from and defined independently of the rotary axis.

12. An X-ray CT scanning method comprising:
providing an X-ray CT scanner comprising: a rotary device comprising an X-ray generator and an X-ray detector opposing to each other, to be provided for interposing an object between them; a rotary mechanism for rotating the rotary device around a rotary axis; a mechanism for moving the rotary axis of the rotary mechanism in two-dimensional directions crossing the rotary axis; and a controller which controls the rotary mechanism and the mechanism for moving the rotary axis, to rotate the rotary device so as to keep a point in a region of interest in the object always at a rotation center in a viewpoint of CT scan different from the rotary axis due to a synthesized motion of the rotation of the rotary device by the rotary mechanism and the movement of the rotary axis by the mechanism for moving the rotary axis; and
changing a distance between the X-ray generator and the rotation center and/or a distance between the X-ray detector and the rotation center to change a magnification.

* * * * *